United States Patent
McGuire et al.

(10) Patent No.: US 10,695,463 B2
(45) Date of Patent: Jun. 30, 2020

(54) MULTI-LAYERED BIOMIMETIC MATERIAL AND METHOD OF FORMATION

(71) Applicant: Clemson University, Clemson, SC (US)

(72) Inventors: Rachel McGuire, Little Mountain, SC (US); Ryan Borem, Easley, SC (US); Jeremy Mercuri, Piedmont, SC (US)

(73) Assignee: Clemson University Research Foundation, Clemson, SC (US)

( * ) Notice: Subject to any disclaimer, the term of this patent is extended or adjusted under 35 U.S.C. 154(b) by 0 days.

(21) Appl. No.: 15/758,528

(22) PCT Filed: Sep. 8, 2016

(86) PCT No.: PCT/US2016/050693
§ 371 (c)(1),
(2) Date: Mar. 8, 2018

(87) PCT Pub. No.: WO2017/044573
PCT Pub. Date: Mar. 16, 2017

(65) Prior Publication Data
US 2018/0228938 A1    Aug. 16, 2018

Related U.S. Application Data

(60) Provisional application No. 62/215,482, filed on Sep. 8, 2015.

(51) Int. Cl.
*A61L 27/36* (2006.01)
*A61L 27/52* (2006.01)
(Continued)

(52) U.S. Cl.
CPC ............ *A61L 27/3633* (2013.01); *A61F 2/08* (2013.01); *A61F 2/442* (2013.01);
(Continued)

(58) Field of Classification Search
CPC ....... A61L 27/3633; A61L 27/36–3695; A61L 27/50; A61F 2002/4495; A61F 2002/4445; A61F 2002/4435; A61F 2/08; A61F 2/442
See application file for complete search history.

(56) References Cited

U.S. PATENT DOCUMENTS 6,969,404 B2   11/2005   Ferree
7,157,428 B2    1/2007   Kusanagi et al.
(Continued)

FOREIGN PATENT DOCUMENTS

EP          1614402        1/2006
WO    WO 2013/116624       8/2013
(Continued)

OTHER PUBLICATIONS

Adams, M. "Biomechanics of Back Pain." *Acupuncture in Medicine* 22(4), (2004), 178-88.
(Continued)

*Primary Examiner* — Brian A Dukert
*Assistant Examiner* — Rebecca Lynee Zimmerman
(74) *Attorney, Agent, or Firm* — Dority & Manning, P.A.

(57) ABSTRACT

Biocompatible biomimetic materials that exhibit desirable mechanical properties while also encouraging cell ingrowth and proliferation are described. The biomaterials include a multi-layer laminate of three or more decellularized aligned collagen tissues. The individual layers are aligned with one another in an angle-ply arrangement, with the collagen of each layer aligned at an angle to the collagen of the adjacent layer. The biomaterials are useful as collagenous graft materials such as a patch for a hernia in an annulus fibrosus or grafting materials for repair of tendons, ligaments, cartilage and other musculoskeletal tissues.

21 Claims, 15 Drawing Sheets

(51) Int. Cl.
*A61L 27/50* (2006.01)
*A61F 2/08* (2006.01)
*A61F 2/44* (2006.01)
*A61F 2/30* (2006.01)

(52) U.S. Cl.
CPC ....... *A61L 27/3604* (2013.01); *A61L 27/3654* (2013.01); *A61L 27/3658* (2013.01); *A61L 27/3662* (2013.01); *A61L 27/3683* (2013.01); *A61L 27/50* (2013.01); *A61L 27/52* (2013.01); *A61F 2002/30009* (2013.01); *A61F 2002/30971* (2013.01); *A61F 2002/4435* (2013.01); *A61F 2002/4495* (2013.01); *A61F 2310/00371* (2013.01); *A61L 2430/06* (2013.01); *A61L 2430/10* (2013.01); *A61L 2430/38* (2013.01)

(56) References Cited

U.S. PATENT DOCUMENTS

| | | | |
|---|---|---|---|
| 7,195,912 | B2 | 3/2007 | Takezawa et al. |
| 7,217,294 | B2 | 5/2007 | Kusanagi et al. |
| 8,137,688 | B2 | 3/2012 | Zahos et al. |
| 8,652,209 | B2 | 2/2014 | Tornier et al. |
| 8,936,642 | B2 | 1/2015 | Ferree |
| 8,945,223 | B2 | 2/2015 | Trieu |
| 9,005,289 | B1 | 4/2015 | Mercuri et al. |
| 9,011,543 | B2 | 4/2015 | Trieu et al. |
| 9,039,769 | B2 | 5/2015 | O'Halloran et al. |
| 2002/0103542 | A1 | 8/2002 | Bilbo |
| 2002/0198599 | A1 | 12/2002 | Haldimann |
| 2004/0059418 | A1 | 3/2004 | McKay et al. |
| 2006/0029639 | A1 | 2/2006 | Morinaga et al. |
| 2007/0041952 | A1 | 2/2007 | Guilak et al. |
| 2007/0093905 | A1 | 4/2007 | O'Neil et al. |
| 2007/0233259 | A1 | 10/2007 | Muhanna et al. |
| 2008/0014179 | A1 | 1/2008 | Ferree |
| 2008/0021563 | A1 | 1/2008 | Chudzik |
| 2008/0065218 | A1 | 3/2008 | O'Neil |
| 2011/0098826 | A1* | 4/2011 | Mauck ............ A61F 2/3094 623/23.72 |
| 2011/0166673 | A1* | 7/2011 | Patel ............ A61L 27/3633 623/23.72 |
| 2012/0221118 | A1* | 8/2012 | Bartee ............ A61L 27/24 623/23.72 |
| 2012/0265300 | A1 | 10/2012 | Mauck et al. |
| 2012/0329156 | A1 | 12/2012 | Cho et al. |
| 2013/0116799 | A1 | 5/2013 | Derwin et al. |
| 2013/0209571 | A1* | 8/2013 | Du ............ C12N 5/0068 424/571 |
| 2016/0243282 | A1 | 8/2016 | Simionescu et al. |

FOREIGN PATENT DOCUMENTS

| | | | | |
|---|---|---|---|---|
| WO | WO 2014/074134 | | 5/2014 | |
| WO | WO-2014074134 A1 | * | 5/2014 | ............ A61L 27/24 |

OTHER PUBLICATIONS

Antoniou et al. "The human lumbar intervertebral disc: Evidence for changes in the biosynthesis and denaturation of the extracellular matrix with growth, maturation, ageing, and degeneration," *J Clin Invest.* 221, (1996), 1153-161.
ASTM. "Standard Test Method for Hydraulic Bursting Strength of Textile Fabrics—Diaphragm Bursting Strength Tester Method," *ASTM International.* (2002).
Atlas, et al. "Long-Term Outcomes of Surgical and Nonsurgical Management of Lumbar Spinal Stenosis: 8 to 10 Year Results from the Maine Lumbar Spine Study," *Spine* 30(8), (2005), 936-943.
Balagué, et al. "Non-specific low back pain." *Lancet* 379, (2012), 482-491.
Boden, et al. "Abnormal Magnetic-Resonance Scans of the Cervical Spine in Asymptomatic Subjects. A Prospective Investigation." *The Journal of Bone and Joint Surgery.* American vol. 72(8). (1990), 1178-84. (Abstract only).
Braga-Vilela, et al. 2008. "Extracellular Matrix of Porcine Pericardium: Biochemistry and Collagen Architecture." *Journal of Membrane Biology* 221(1), (2008), 15-25.
Bron, et al. "Repair, Regenerative and Supportive Therapies of the Annulus Fibrosus: Achievements and Challenges." *European Spine Journal* 18(3), (2009), 301-13.
Carragee, et al. "Clinical Outcomes after Lumbar Discectomy for Sciatica: The Effects of Fragment Type and Anular Competence," *The Journal of Bone and Joint Surgery.* American 85-A(1), (2003), 102-8.
Chan, et al. "Decellularized bovine intervertebral disc as a natural scaffold for xenogenic cell studies." *Acta Biomater.* 9, (2013), 5262-72.
Cloyd, et al. "Material properties in unconfined compression of human nucleus pulposus, injectable hyaluronic acid-based hydrogels and tissue engineering scaffolds." *Eur. Spine J.* 16, (2007), 1892-1898.
Crapo, et al. "An Overview of Tissue and Whole Organ Decellularization Processes." *Biomaterials* 32(12), (2011), 3233-43.
Deyo, R. "In Project Briefs: Back Pain Patient Outcomes Assessment Team (BOAT)." *Agency for Healthcare Research and Quality.* (1994).
Freeman, et al. "Compressive properties of fibrous repair tissue compared to nucleus and annulus." *J. Biomech.* 46, (2013), 1714-1721.
Freytes, et al. "Analytically Derived Material Properties of Multilaminated Extracellular Matrix Devices Using the Ball-Burst Test." *Biomaterials* 26(27), (2005), 5518-31.
Gilbert, et al.. 2009, "Quantification of DNA in Biologic Scaffold Materials." *The Journal of Surgical Research* 152(1), (2009), 135-39.
Green, et al. "Tensile Properties of the Annulus Fibrosus II. Ultimate Tensile Strength and Fatigue Life," *European Spine Journal* 2, (1993), 209-14. (Abstract only).
Guterl, et al. "Challenges and Strategies in the Repair of Ruptured Annulus Fibrosus." *European Cells & Materials* 25, (2013), 1-21.
Holzapfel, et al., "Single lamellar mechanics of the human lumbar anulus fibrosus," *Biomech. Model Mechanobiol.* 3(3), (2005), 125-140.
Hu, et al. "A Population-Based Study of Reoperations After Back Surgery," *Spine* 22(19), (1997), 2265-2270.
Hughes, et al. "The Pathogenesis of Degeneration of the Intervertebral Disc and Emerging Therapies in the Management of Back Pain." *The Journal of Bone and joint Surgery.* British vol. 94(10), (2012), 1298-1304.
Jensen, et al. "Magnetic Resonance Imaging of the Lumbar Spine in People without Back Pain," *N Engl J Med* 331, (1994), 69-73.
Lequin, et al. "Primary Limited Lumbar Discectomy with an Annulus Closure Device: One-Year Clinical and Radiographic Results from a Prospective, Multi-Center Study," *Korean Spine* 9(4), (2012), 340-347.
Long, et al. "Mechanical Restoration and Failure Analyses of a Hydrogel and Scaffold Composite Strategy for Annulus Fibrosus Repair." *Acta Biomaterialia* 30, (2015), 116-25.
Martin, et al. "Expenditures and health status among adults with back and neck problems," *JAMA* 299, (2008), 656-664.
Mercuri, et al. "Regenerative potential of decellularized porcine nucleus pulposus hydrogel scaffolds: stem cell differentiation, matrix remodeling, and biocompatibility studies." *Tissue Eng. Part A* 19, (2013), 952-66.
Mercuri, et al. "Novel tissue-derived biomimetic scaffold for regenerating the human nucleus pulposus." *J. Biomed. Mater. Res.—Part A* 96 A, (2011), 422-435.
Mow, et al., "Basic Orthopedic Biomechanics." Philadelphia: Lippincott-Raven (1997).
Mwale, et al. "Distinction between the extracellular matrix of the nucleus pulposus and hyaline cartilage: a requisite for tissue engineering of intervertebral disc." *Eur Cell Mater* 8 (2004), 58-64.

(56) References Cited

OTHER PUBLICATIONS

Nerurkar, et al. "Nanofibrous Biologic Laminates Replicate the Form and Function of the Annulus Fibrosus," *Nature Materials* 8(12), (2009), 986-92.
O'Connell, et al. "Human Annulus Fibrosus Material Properties from Biaxial Testing and Constitutive Modeling Are Altered with Degeneration." *Biomechanics and Modeling in Mechanobiology* 11(3-4), (2012), 493-503.
Praemer, et al. "Musculoskeletal conditions in the United States." *Am Acad Orthop Surg*. (1999), 85-124.
Rémi, et al. "Pericardial Processing: Challenges, Outcomes and Future Prospects." *Biomaterials Science and Engineering*, (2011), 437-57.
Schoenfeld, et al. "Treatment of Lumbar Disc Herniation: Evidence-Based Practice." *International Journal of General Medicine* (3), (2010), 209-14.
Smith, *J Bone Joint Surg Br*. (1951).
Tedder, et al. "Stabilized Collagen Scaffolds for Heart Valve Tissue Engineering," *Tissue Engineering, Part A* 15(6), (2009), 1257-68.
Urban, et al. "Degeneration of the Intervertebral Disc." *Arthritis Res Ther* 5(3), (2003), 120.
Urban, et al. "The Nucleus of the Intervertebral Disc from Development to Degeneration." *American Zoologist* 40(1), (2000), 53-61.
Vallfors, B. "Acute, Subacute and Chronic Low Back Pain: Clinical Symptoms, Absenteeism and Working Environment." *Scan J Rehab Med Suppl* 11, (1985), 1-98. (Abstract only).
Wilke, et al. "New in Vivo Measurements of Pressures in the intervertebral Disc in Daily Life." *Spine* 24(8), (1999), 755-62.
PCT International Search Report & Written Opinion, PCT/US/16/50693, (dated 2016).
McGuire, R.M. "The Development of a Biomimetic Patch for Annulus Fibrosus Repair" *Clemson University* (published May 2016) pp. 1-76.

* cited by examiner

MULTI-LAYERED BIOMIMETIC MATERIAL AND METHOD OF FORMATION

CROSS-REFERENCE TO RELATED APPLICATIONS

This application claims filing benefit of U.S. Provisional Patent Application Ser. No. 62/215,482 having a filing date of Sep. 8, 2015, which is incorporated herein by reference in its entirety.

BACKGROUND

Annually, over 5.7 million Americans are diagnosed with intervertebral disc disorders. As shown in FIG. 1, an intervertebral disc 12 includes the nucleus pulposus 10 surrounded by the annulus fibrosus 16. A disc 12 forms a cushion between adjacent vertebrae 14 and supports compressive loads during activities of daily living. Intervertebral disc disorders include intervertebral herniation (a mechanical disruption of the annulus fibrosus) and degeneration (which initiates within the nucleus pulposus). These pathologies can lead to a loss in disc height, impaired mechanical function, and long-term pain and disability.

Current therapies for both intervertebral disc degeneration and herniation are palliative and often only delay invasive surgical management in the form of discectomy, spinal fusion or total disc replacement. While these procedures may temporarily relieve pain, they do not attempt to replace, restore or regenerate damaged tissue with healthy biological tissue. Moreover, surgical approaches can provide long term solution to particular problems, but there are concerns with the use of surgical methodologies that may promote re-herniation, altered spinal biomechanics, and accelerated degeneration in adjacent discs.

The annulus fibrosus is an oriented lamellar structure with unique properties that are not easily matched. The unique hierarchical structure provides the mechanical strength necessary for physiologically function. Mechanically, the annulus fibrosus is highly anisotropic, heterogeneous, and non-linear and serves the dual mechanical roles of restraining nucleus pulposus intradiscal pressure and connecting adjacent vertebrae. Various suturing techniques, adhesives, and natural and synthetic biomaterials have been developed in an attempt to provide materials and methods for functional repair of annulus fibrosus herniation and/or degeneration. While some of these approaches have demonstrated an amount of success toward cell adhesion, proliferation, and extra cellular matrix (ECM) production, none have illustrated comparable structural and mechanical characteristics of the native annulus fibrosus concomitant with the ability to support tissue regeneration. For instance, simply suturing herniation in annulus fibrosus tissue does not adequately fill the voids left by the original tissue damage, bioadhesives have not proven strong enough to adequately withstand the mechanical environment of the annulus fibrosus, occlusive mesh implants have likewise not met the necessary mechanical strength standards, and materials that can provide high mechanical strength, such as certain electrospun materials, are not cost effective and present serious scalability issues. In particular, no biomaterial has been developed that can effectively mimic the angle-ply collagen architecture and mechanical properties of the native annulus fibrosus while supporting natural cell ingrowth and proliferation.

What is needed in the art is a biomimetic biomaterial that can be utilized in intervertebral disc herniation or degeneration repair, among other applications, that can provide both structural characteristics to provide high functionality and cellular compatibility to encourage development of healthy tissue in the implant area. Furthermore, it would be beneficial to devise a simple, scalable process by which to manufacture the biomimetic biomaterial.

SUMMARY

According to one embodiment, disclosed is a biocompatible construct that includes a first, second and third layer. Each of these three layers includes a decellularized tissue that includes collagen in a generally aligned orientation. In addition, the layers are arranged such that the directions of the collagen alignment in adjacent layers are offset from one another. For instance, the first layer can include collagen generally aligned in a first direction, and the second layer can include collagen generally aligned in a second, different direction such that an angle is defined between the first direction and the second direction. This angle can vary depending upon the specific application of the construct. For instance, this angle can generally be from about 25° to about 90° for an annulus fibrosus repair, and can be less for a musculoskeletal construct such as a tendon or ligament repair, for instance about 25° or less. The third layer can be adjacent to the second layer (i.e., the second layer can be between the first and third layers). The collagen of the third layer can be generally aligned in a third direction that is offset from the alignment direction of the collagen of the second layer so as to define a second angle between the second direction and the third direction that can generally be in the same range as the angle between the first and second direction. In addition, the collagen alignment direction of the first layer can be essentially the same as the collagen alignment direction of the third layer.

The layers of the construct can be attached to one another, for instance by suturing or an adhesive, to form a multi-layer laminate that exhibits excellent biocompatibility and mechanical characteristics. In one embodiment, the multi-layer laminate can be utilized as a patch for an annulus fibrosus. The construct can be utilized in other applications as well, for instance as a graft for a ligament or tendon.

Also disclosed is a method of forming a biocompatible construct that can include locating three decellularized tissue sheets adjacent one another such that the alignment directions of the collagen of the sheets are offset as described, and then attaching the sheets to one another.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures, in which:

FIG. 11 also presents a schematic representation depicting histology sectioning of the construct using an oblique cutting plane (dotted line) across multiple layers to microscopically visualize collagen fiber alignment in fibrous pericardium surfaces stacked directly adjacent to one another demonstrating a ±30° "chevron" pattern. Also shown is the cross sectional result when fibrous and parietal pericardium surfaces are directly adjacent to each other and a "half chevron" pattern is achieved.

DETAILED DESCRIPTION

Figure 1:
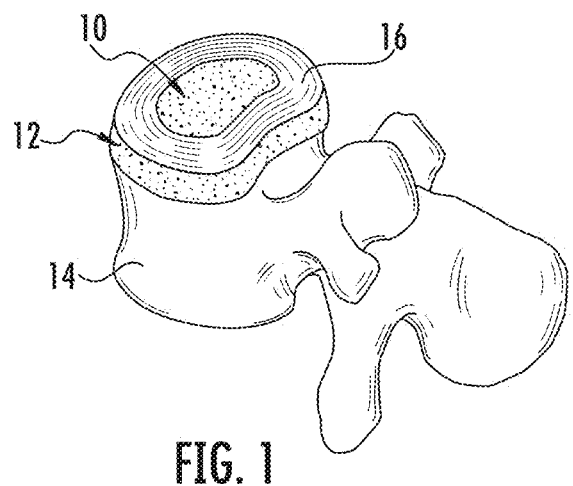
FIG. 1 illustrates a typical intervertebral disc and associated vertebrae.

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment, may be used in another embodiment to yield a still further embodiment. Thus, it is intended that the present disclosure cover such modifications and variations as come within the scope of the appended claims and their equivalents.

In general, the present disclosure is directed to biocompatible biomimetic materials that exhibit desirable mechanical properties while also encouraging cell ingrowth and proliferation. In one particular embodiment, the biomaterials can provide a route to early-stage interventional strategies to treat intervertebral disc degeneration and herniation and prevent re-herniation in patients with large annulus fibrosus defects. In particular, the biocompatible materials can be utilized as a patch for rupture in an annulus fibrosus due to herniation or intended surgical procedures. In addition, the biomaterials can serve as a platform to develop full-thickness annulus fibrosus and whole intervertebral disc tissue engineering strategies. In other embodiments, the biomaterials can be useful as strong graft materials for damaged collagenous tissues such as tendons, ligaments, cartilage and other strong, fibrous connective musculoskeletal tissues.

As mentioned previously, one major limitation of intervertebral disc repair is that no biomaterial has been developed which effectively mimics the angle-ply collagen architecture and mechanical properties of the native annulus fibrosus while also exhibiting desirable cell support characteristics. The disclosed materials solve this problem through formation of a multi-layer angle-ply construct derived from decellularized tissue. The individual plies of the construct are arranged to provide an angle-ply microarchitecture that mimics the natural architecture of the annulus fibrosus. As such, the biomaterials can exhibit mechanical characteristics such as biaxial burst strength and tensile properties that approach or match the native tissue.

The average tensile strength of a multi-layer construct can meet or exceed the reported values of the native human annulus fibrosus tissue. For instance, a multi-layer construct can exhibit a biaxial burst pressure of about 2 megapascals (MPa) or greater, or about 4 MPa or greater in some embodiments, and can exhibit a biaxial impact level of about 0.2 MPa or greater, for instance about 0.4 MPa or greater, or about 0.8 MPa or greater in some embodiments. Similarly, the burst pressure of the biomaterials can meet or exceed that of natural tissue. For example, a multi-layer construct can exhibit a burst pressure of about 3 MPa or greater, about 5 MPa or greater, about 10 MPa or greater, or about 15 MPa or greater in some embodiments. Burst and impact strength of the biomaterials can provide capability to withstand forces expected during use following implant. For instance, disclosed materials can withstand intradiscal pressures typically seen within the human intervertebral discs.

In addition, a construct can exhibit a high ultimate tensile strength (UTS) due to the collagen fibers' mechanical ability to resist tension. When decellularized aligned collagen tissues are arranged in angle-ply laminates as described they can demonstrate high UTS similar to or higher than values seen in natural annulus fibrosus tissue. This occurs due to the complex hierarchical tissue structure which is also consistent with literature of testing of angle-ply laminates. For example, the multi-layer constructs can exhibit UTS of about 3 MPa or greater, about 4 MPa or greater, or about 5 MPa or greater in some embodiments.

The elastic modulus of a construct can fall within the range of the tissue for repair by use of the construct. For instance, a construct can exhibit an elastic modulus similar to that of human annulus fibrosus tissue, e.g., from about 12 MPa to about 24 MPa in some embodiments.

The constructs can also exhibit a high tensile strain at break, which can allow for the materials to maintain integrity through a large strain range. For instance, the biomaterial tensile strain at break values can be comparable to the amount of strain experienced when a patient is in full flexion, e.g., about 55% or greater in some embodiments. In addition, the biomaterials can exhibit a stress to cycle number tensile fatigue curve (S/N curve) profile prior to failure similar to human tissues.

In addition to the excellent mechanical characteristics, and as the biomaterial constructs are based on decellularized natural materials, they can exhibit excellent cytocompatibility with surrounding tissue upon implant and with cells that can be seeded on the materials. Moreover, the constructs can be essentially free of immunogenic components of the source materials from which they can be formed, and as such can be safe for implant and exhibit excellent regenerative capacity.

Figure 2:
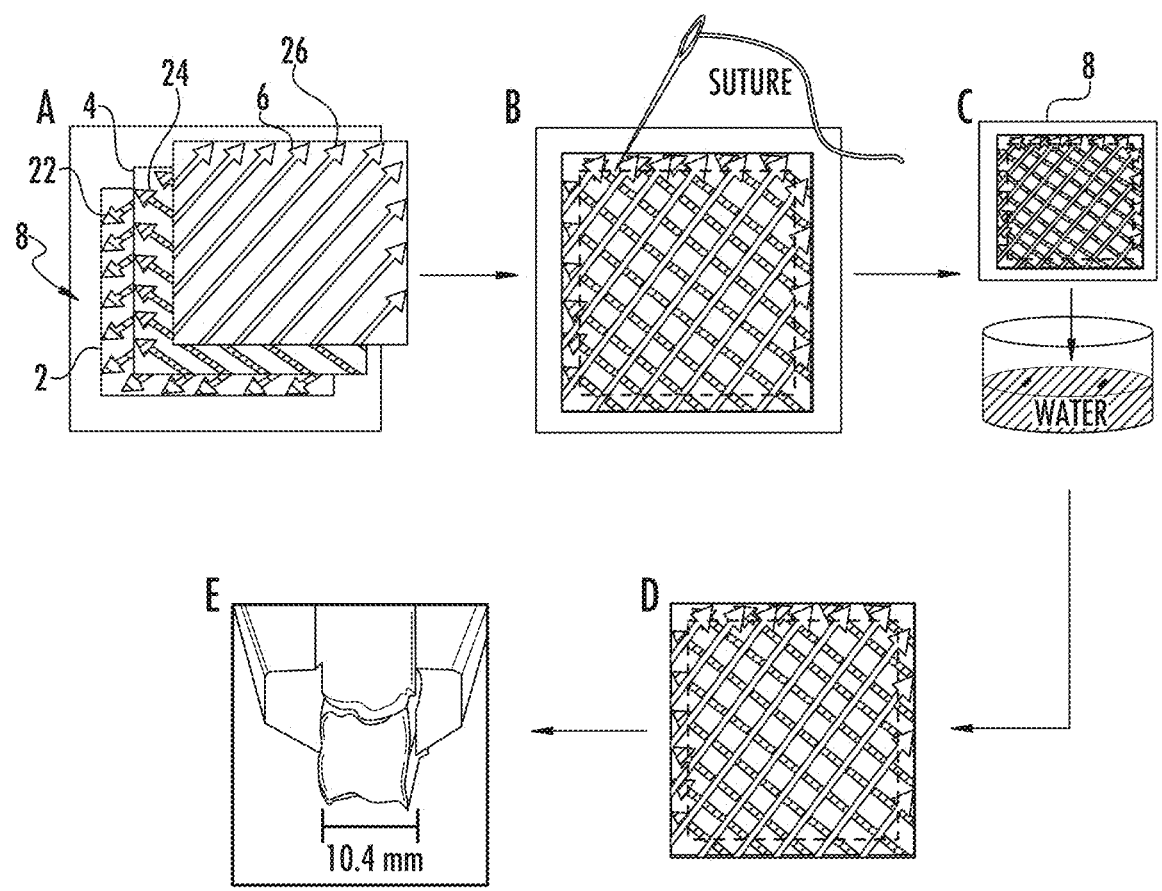
FIG. 2 is a schematic representation of a process for forming a construct as described herein.

As illustrated in FIG. 2 at panel A, a multi-layer laminate construct can include at least three sheets 2, 4, 6 arranged together in a layered fashion. The sheet(s) can be developed from any autogenic, allogenic, or xenogenic source tissue that includes elastin and collagen in which the collagen fibers of at least one layer of the source tissue are generally aligned with one another and with a surface of the tissue, i.e., an aligned collagen tissue. As utilized herein, the term "aligned collagen tissue" generally refers to a tissue that includes at least one layer within which the collagen fibers are generally aligned with a surface of the tissue and with one another. As is known, the specific hierarchical organization of collagen molecules determines the unique properties of each specific collagen-containing tissue. For example, in tendon, the high density and parallel alignment of collagen molecules, fibrils, fibers, fascicles and tendon units gives tendon its unique mechanical properties. In the present case, an aligned collagen tissue can be considered to be a tissue in which about 75% or more of the collagen fibers of a single layer of the tissue are aligned within about 20° or less of one another. The source tissue can include other layers that are substantially collagen-free or that include collagen in a random or isotropic orientation.

By way of example, and without limitation, sheets of the multi-layer construct can be developed from vascular tissue (e.g., aortic tissue, vena cava tissue), tendons, ligaments, dermal tissue, pericardial tissue, dura mater, umbilical tissue, fascia, submucosal tissue, amniotic tissue, etc. In one embodiment, all of the layers of a multi-layer construct can be formed from the same source tissue type, but this is not a requirement and in other embodiments, one or more of the layers can be formed of different source materials.

Collagen and elastin are the fibrous components of connective tissue that provide structural support, strength, and elasticity to the tissue. Elastin is the protein constituent of connective tissue responsible for the elasticity and recoil of tissues, while collagen provides both strength and structural characteristics to tissues. The relative proportion of collagen and elastin in connective tissue will vary depending upon the function of the tissue. For instance, elastin is the most abundant extracellular matrix protein found in the aortic wall, while collagen is the primary extracellular matrix protein in stronger, less flexible tissues such as cartilage, tendons, and ligaments. Source tissue for forming disclosed biomaterials can be selected based upon the final application of the biomimetic materials. For instance, a biomaterial intended for use in an application that requires high flexibility can be formed with a source tissue having a relatively high elastin content (e.g., vascular tissue) while a biomaterial intended for use in a high strength but low flexibility application may be formed from a source tissue that includes a relatively lower elastin content (e.g., musculoskeletal tissues). In any case, a source tissue can be an aligned collagen tissue in which at least one layer of the source tissue includes collagen that is generally aligned in a determinable direction. Beneficially the collagen and elastin of the source tissue can function as fibrous reinforcement throughout the biomaterial formed from the tissue, and the aligned collagen of the individual layers combined with the angled relationship of the collagen between adjacent layers can provide excellent mechanical characteristics to the biomaterials.

In one embodiment, pericardium, the connective tissue that surrounds the heart, can serve as source material for construction of a multi-layer angle-ply biomimetic biomaterial. Pericardium is a durable, thin sheet including an aligned collagen fiber-reinforced matrix that has been extensively used in the manufacture of medical devices including bioprosthetic heart valves and tendon grafts. The pericardium itself is comprised of both dense regular and irregular connective tissue (predominantly type I collagen) that is organized into fibrils, fibers, fiber bundles and laminates. The fibrous pericardium is the outermost later of the pericardium and contains aligned type I collagen fibers. This outer layer is fused to an adjacent layer of parietal pericardium that contains a multi-directional network of fine collagen fibers and elastin. Even when combined with the multi-directional network of the parietal pericardium, the predominant global fiber directionality of the fibrous pericardium is evident when examining the multi-layer structure of the pericardium. Thus, in one embodiment, a biomaterial construct can include multiple sheets of decellularized pericardium (each of which containing one or more layers) that are oriented relative to each other and overlaid such that the fiber alignment of the fibrous pericardium of each layer can be tailored as desired. The resulting multi-layer laminate can achieve varying angle-ply orientations and mechanical properties similar to the tissue that is intended to be repaired by use of the construct, and in one particular example, similar to human annulus fibrosus tissue.

To increase the biocompatibility of the biomaterial, the source tissue(s) can be treated to remove immunogenic materials. For instance, the source tissue can be treated according to any known method to decellularize the source tissue. One exemplary method for decellularization of connective tissue has been previously described by Tedder, et al. (Tissue Engineering: Part A, 2009, 15(6), 1257-1268). Briefly, the treatment process can include cell lysis by hypotonic shock followed by treatment with a detergent decellularization solution that can include, e.g., sodium-deoxycholate, Triton® X-100, ethylenediaminetetraacetic acid (EDTA), sodium azide, etc., or combinations thereof. Following, the source tissue can be treated with nucleases to fully digest nucleic acids of the source tissue.

Through decellularization of the source tissue so as to remove immunogenic factors from the tissue, a highly biocompatible sheet can be formed that can support human cell viability, proliferation and growth. This can not only reduce or eliminate rejection potential of the biomaterial following implantation, but can improve long-term integration of the implanted biomaterial with surrounding tissue and increase the likelihood of long-term repair of the repaired tissue, rather than providing merely palliative care as is currently the most common treatment option for a herniated disc.

To enhance strength of the biomaterial, a plurality of at least 3 sheets can be layered together with the fibrous ply of each individual sheet at an angle to that of an adjacent sheet that can approximate the angled collagen arrangement of the natural tissue. For instance, multiple sheets can be assembled into a ply-angle-ply orientation to match (or nearly match) the characteristics of the native architecture of the surrounding annulus fibrosus following implantation. The angle between adjacent sheets can be the angle formed between directional lines that indicate the directional orientation of the collagen of each sheet. For example, and with reference to FIG. 2, panel A, a first sheet 2 can be supported on a substrate 8, which can, in one embodiment, be a dissolvable tissue backing as is generally known in the art.

The first sheet 2 can include collagen that is generally aligned in a direction as indicated by the directional arrows 22. A second sheet 4 can be located adjacent to the first sheet 2 and can include collagen that is generally aligned in a direction as indicated by the directional arrows 24. When forming a construct for use with an intervertebral disc such as an annulus fibrosus repair, the directional arrows 22 and the directional arrows 24 can be offset from a common horizontal (not shown on FIG. 2) by a rotational angle of from about 12° to about 45°, or from about 15° to about 45° in some embodiments. Thus, the angle between the directional arrows 22 and the directional arrows 24 can be from about 25° to about 90°, from about 30° to about 90°, or from about 35° to about 65° in some embodiments.

The construct can also include a third sheet 6 that includes collagen aligned in a general direction as indicated by the directional arrows 26. The third sheet 6 can be located on the construct such that the directional arrows 26 generally align with the directional arrows 22 of the first sheet and with the second sheet 4 located between the first and third sheets 2, 6. Thus, the angle between the directional arrows 26 of the third sheet 6 and the directional arrows 24 of the adjacent second sheet 4 can be from about 25° to about 90° or from about 35° to about 65° in some embodiments.

The angles defined between the collagen orientation directional lines (or arrows in the illustrated case of FIG. 2) of adjacent sheets can be modified as desired such that the multi-layer construct more closely mimics the microarchitecture of the native material to which it is intended to be applied. For instance, when forming an annulus fibrosus graft material, the angle between the collagen orientation directions of adjacent sheets can be from about 25° to about 90°, from about 50° to about 70°, or about 60° in some embodiments (e.g., each directional line being from about ±25° to about ±35°, or about ±30° from a common horizontal).

In other embodiments, the angled relationship of the collagen between adjacent plies can be varied to more closely approximate the angled relationship of collagen across the depth of the natural tissue to which the implant will be attached. For instance, when considering a musculoskeletal graft, such as a tendon graft, the angle between the collagen orientation directions of adjacent sheets can be less than that found in annulus fibrosus grafts such as, for example, about 25° or less, or from about 5° to about 20° in some embodiments.

Other characteristics of the individual sheets and/or the multi-layer laminate material may also be adjusted as desired so as to provide desired characteristics to the multi-layer construct. For instance, the thickness of a single sheet can vary depending upon the source tissue utilized to form the sheet, the processing conditions used, etc. In one embodiment, a single sheet can have an average thickness of between about 20 micrometers (μm) and about 300 μm, for instance between about 30 μm and about 290 μm, or between about 150 μm and about 270 μm.

As shown at FIG. 2, panel B, following proper alignment, a plurality of sheets 2, 4, 6 can be aligned with one another and adhered to one another. For example, in the illustrated embodiment, the sheets can be sutured together. Suturing is not a requirement of the methods, however, and any suture material, adhesive and attachment method as is known in the art can be utilized. For instance, in one embodiment, a dissolvable suture can be utilized that can dissolve over time following implantation and as the biomaterial becomes integrated with surrounding tissue. Any bioadhesive or combination thereof as is known in the art can alternatively be utilized to attach the individual sheets to one another.

When formed on a backing material, the backing can be removed prior to implantation. For instance, as illustrated at FIG. 2, panel C, a dissolvable backing material 8 can be removed by immersion of the multi-layer construct in water for a period of time, thereby forming a self-supported multi-layer construct, as shown FIG. 2, panels D and E.

While one of the major hurdles to regeneration of damaged annulus fibrosus tissue is to promote the development the highly oriented multi-layer structure, a biomaterial that can successfully assist the repair/regenerative process must also have the appropriate dimensions, for instance to effectively address large annulus fibrosus hernias while conforming to the site of implantation. For instance, an annulus fibrosus repair construct may need to cover defects on the order of 6-6.5 mm at the widest dimension and will need to accurately overlay the damaged outer annulus fibrosus tissue on lumbar intervertebral discs, which can have anterior and posterior heights ranging from 4-14 mm. Beneficially, disclosed formation methods can successfully meet these difficulties, as provided is a method for formation of a construct of any necessary size. By way of example, a multi-layer construct can have a surface area of about 300 mm$^2$, or even larger in some embodiments. For instance, a multi-layer construct for use as an annulus fibrosus patch can be formed with a surface area of from about 4 mm×4 mm to about 15 mm×15 mm in some embodiments that can meet the design requirements for use in either the anterior or posterior annulus fibrosus by virtue of their micro-architecture and customizable dimensions.

In general, a multi-layer construct can be porous and as such can allow for the influx and efflux of biomolecules such as lower molecular weight molecules including but not limited to water, glucose, cytokines, and growth factors. Moreover, and depending upon the porosity of the biomaterial, the biomaterials can allow for the movement of cells, e.g., either influx of host cells and/or efflux of cells implanted in conjunction with the material, which can aid in integration of the biomaterial with surrounding tissue as well as aiding with regeneration of the natural structure, e.g., the annulus fibrosus.

In one embodiment, the fibrous components of the biomaterial construct can be cross-linked with collagen and/or elastin cross-linking agents to further enhance the construct. Cross-linking can be utilized to affect multiple characteristics of a construct. For example, the level of cross-linking can influence the porosity and various strength characteristics of the multi-layer construct. Cross-linking of the biomaterial can also be utilized to control the degradation characteristics of the material following implantation. Degradation of collagen is a naturally occurring phenomenon prevalent in intervertebral disc pathology. Collagen is rapidly broken down by collagenases, known as MMPs, produced in the area. Accordingly, crosslinking of a construct can be of benefit to slow the natural degradation processes of the material particularly when considering the constructs for use as an annulus fibrosus biomaterial implant.

Any suitable crosslinking agent can be utilized. For example, collagen fixatives such a glutaraldehyde, carbodiimide, polyepoxides, etc. and/or elastin fixatives including polyphenolic compounds (tannic acid, pentagalloyl glucose, etc.) and the like can be utilized to cross-link the structural proteins of the multi-layer construct.

The multi-layer construct can be further processed to provide desired characteristics to a product. For instance, in one embodiment, a secondary material, such as a hydrogel or solution can be incorporated between one or more of the adjacent layers. For instance a hydrogel that includes natural extracellular matrix components (i.e. glycosaminoglycan based gel, a collagen based gel) or a synthetic polymer based gel can be located between adjacent layers, either between only two of the layers or between more of the layers, and between all of the layers in one embodiment. Materials between adjacent layers can be useful for carrying or delivery cells or desirable biologically active materials. Intra-layer materials can, for example, promote integration with adjacent tissues, promote cell migration, provide drug delivery, etc. An intra-layer material can also be designed to affect mechanical shearing between layers, and can improve mechanical durability of the laminate construct.

Hydrogels as may be incorporated between layers of a construct can include any biocompatible polymeric matrix that can be highly hydrated while maintaining structural stability. Suitable hydrogel matrices can include noncrosslinked and crosslinked hydrogels. In addition, crosslinked hydrogels can optionally include hydrolyzable portions, such that the matrix can be degradable when utilized in an aqueous environment, e.g., in vivo. For example, a construct can include between one or more adjacent layer pairs a cross-linked hydrogel including a hydrolyzable cross-linking agent, such as polylactic acid, and can be degradable in vivo.

A hydrogel can include natural polymers such as glycosaminoglycans, polysaccharides, proteins, and the like, as well as synthetic polymers, as are generally known in the art. A non-limiting list of hydrophilic polymeric materials that can be utilized in forming a hydrogel can include dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

A hydrogel can be formed according to any method as is generally known in the art either prior to or following location of the materials between adjacent layers of a construct. For instance, the hydrogel can self-assemble upon contact of the various components or upon contact in conjunction with the presence of particular environmental conditions (such as temperature or pH) prior to or following location of the hydrogel (or components thereof) between adjacent layers. Alternatively, assembly can be induced according to any known method following combination of the components. For example, step-wise or chain polymerization of multifunctional monomers, oligomers, or macromers can be induced via photopolymerization, temperature dependent polymerization, and/or chemically activated polymerization. Optionally, the hydrogel can be polymerized in the presence of an initiator. For example, the hydrogel can be photopolymerized in the presence of a suitable initiator such as Irgacure® or Darocur® photoinitiators available from Ciba Specialty Chemicals. In another embodiment, a cationic initiator can be utilized such as $Ca^{2+}$, $Mg^{2+}$, $Al^{3+}$, $La^{3+}$, or $Mn^{2+}$ can be used. In another embodiment, a polycationic polypeptide such as polylysine or polyarginine can be utilized as an initiator.

The components of the hydrogel can be self-assembling. For example, hydrogel precursor materials can be located between adjacent layers, for instance via injection, and the hydrogel matrix can self-assemble at physiological conditions following implant. For instance, the hydrogel precursor materials can include self-assembling biopolymers such as collagens, laminins, pro-elastin peptides, and the like. Optionally, a self-assembling hydrogel precursor can include synthetic polymers that can array themselves according to domains, as is generally known in the art. For example, hydrophilic, relatively charge-neutral synthetic polypeptides such as polyglycine or polylysine can be modified to function in this capacity. Polypeptides can be crosslinked by using carboxy-activating crosslinking agents such as water-soluble carbodiimides. Such cross-linking agents can be used to attach self-assembling proteins or other self-assembling macromolecules to the polypeptides. One example of this approach includes formation of a carbodiimide linkage of collagen or laminin with polylysine. Other hydroxylated entities can be linked in a similar manner. For example, in one embodiment, polyvinyl alcohol can be linked with polypeptides using an epoxy-activation approach or crosslinked via polymerizable methacrylate groups along its side chains, as is known in the art.

In another embodiment, a self-assembling hydrogel can be generated by use of precursors that have been derivatized to contain favorably reactive groups. For example, a hydrogel of this type could be assembled using a first precursor derivatized with a particular reactive moiety and a second precursor derivatized with or comprising a second moiety that can preferentially react with the first moiety on the first precursor. Likewise, other such hydrogels could be generated using such reactive pairs wherein the two moieties that react to form the bond are each conjugated to the same or a different type of polymer. For example, the pairs can be antibody-antigen pairs or avidin-biotin (e.g. streptavidin-biotin).

Figure 3:
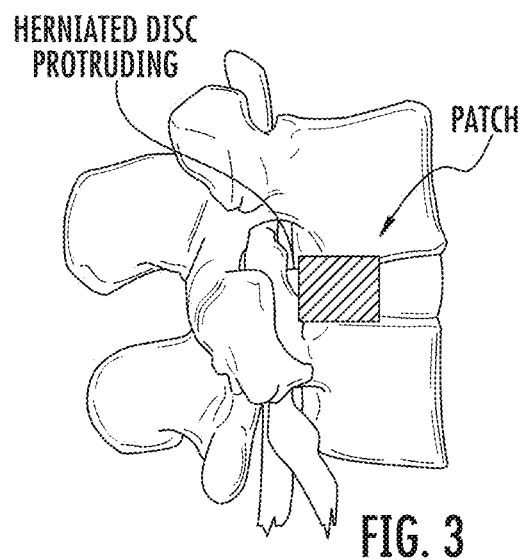
FIG. 3 illustrates one method of use of a construct.

In one embodiment, the construct can be further processed so to modify the outer surface of the multi-layer construct, for instance to enhance adhesion to and/or integration with the surrounding material, which can also decrease the likelihood of shifting of the construct following implantation. For instance, when employing a multi-layer construct as an annulus fibrosus patch, an example of which is illustrated in FIG. 3, a surface of a construct can be augmented with one or more tissue adhesives to enhance adhesion to the annulus fibrosus following implantation. Alternatively, the patch can be sutured to existing native annulus fibrosus tissue with no additional bioadhesive.

The multi-layer construct can be loaded with one or more biologically active agents such as, without limitation, analgesics, anti-apoptotic agents, antibiotics, anti-inflammatory agents, etc. In one embodiment, a multi-layer construct can be loaded with an agent that can be particularly selected for the application, for instance an agent designed to ameliorate intervertebral disc degeneration.

Biologically active compounds as may be incorporated in or on the surface of a construct can include, without limitation, tissue inhibitors of matrix metalloproteinases (TIMPS), growth factors such as transforming growth factor β, bone morphogenetic proteins, fibroblast growth factor, epithelial growth factor, etc. In one particular embodiment, the construct can be seeded with cells, e.g., stem cells, so as to encourage regeneration of the local area following implant of the construct.

The individual sheets of a multi-layer construct can be modified with varying amounts of biologically active agents. For instance, different amounts of cell attracting agents such as, without limitation, glucose, serum proteins, chemokines, peptides, etc. can be included in different amounts on different individual sheets of the material so as to create a gradient that can entice host cells to enter into the (e.g., higher concentration of attractant molecules on the inside layers and lower concentration of attractant molecules in the outer layers of the biomaterial can draw cells toward one side of the biomaterial, e.g., toward the nucleus pulposus). This can encourage integration of the biomaterial with the surrounding tissue following implantation.

The multi-layer construct can be modified to include other compounds that may serve other purposes as desired. For instance, a multi-layer construct can be modified to include radio-opaque agents such that the biomaterial can be visualized with traditional medical imaging technology during and/or following implantation of the construct.

The angle-ply multi-layer construct can be formed using a simple and scalable process resulting in a biomaterial that demonstrates structural and mechanical properties comparable to that of native tissue an in one particular embodiment, comparable to human annulus fibrosus tissue. Furthermore, the multi-layer construct can support the viability and proliferation of cells thus provided excellent regenerative potential. Taken together, the potential clinical value of the multi-layer constructs, for instance for patients undergoing surgical procedures for intervertebral disc herniation is immense.

The present disclosure may be better understood with reference to the Examples, presented below.

EXAMPLE 1

Porcine pericardium was obtained from a local abattoir and transported within three hours of harvest. Tissue was cleaned of extraneous fat and subjected to a decellularization process previously described by Tedder et al, with modification (Tedder et al. 2009). Briefly, pericardium was submerged in distilled water for 24 hours at 4° C. to lyse porcine cells via hypotonic shock. Tissue specimens (3 pieces ~2×5 cm each) were then transferred to 100 ml decellularization solution (pH 7.8) containing 50 mM Tris, 0.15% (v/v) Triton X-100, 0.25% (w/v) deoxycholic acid, 0.1% (w/v) EDTA and 0.02% (w/v) sodium azide while maintained at room temperature under constant agitation (150 RPM) for 3 days. The decellularization solution was changed on day 3 and the process was continued for a total of 6 days prior to sequential washes in 70% ethanol and distilled water (two washes each for 10 minutes while agitating at room temperature). Tissues were placed in a solution (pH 7.5) of DNase/RNase (720U/ml each) containing 5 mM magnesium chloride at 37° C. for 24 hours at 150 RPM.

Decellularized samples were evaluated histologically (5 μm sections) for tissue micro-architecture, extracellular matrix component identification and for the confirmation of porcine cell nuclei removal via hematoxylin and eosin (H&E; n=6) and Movat's Pentachrome (n=6) stains for the evaluation of cell nuclei as well as agarose gel electrophoresis and Nanodrop spectrophotometry for residual porcine DNA which was isolated from tissue via a Qiagen DNeasy Blood and Tissue kit according to manufacturer's instructions. Additionally, immunohistochemistry (IHC) for the porcine antigenic epitope alpha-gal was performed.

Figure 4:
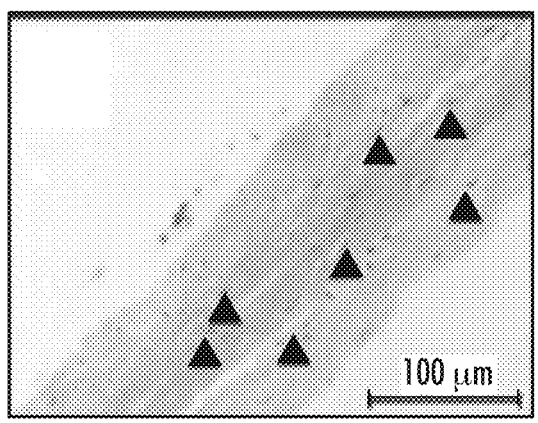
FIG. 4 is a histological image of fresh porcine pericardium stained with H&E (arrowheads=location of cell nuclei) (total magnification: 200×).
Figure 5:
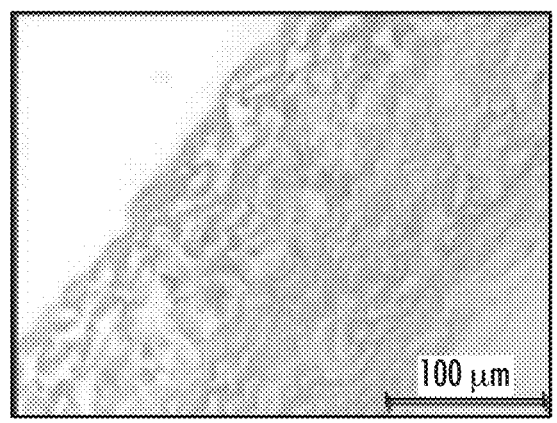
FIG. 5 is a histological image of decellularized porcine pericardium stained with H&E (total magnification: 200×).
Figure 6:
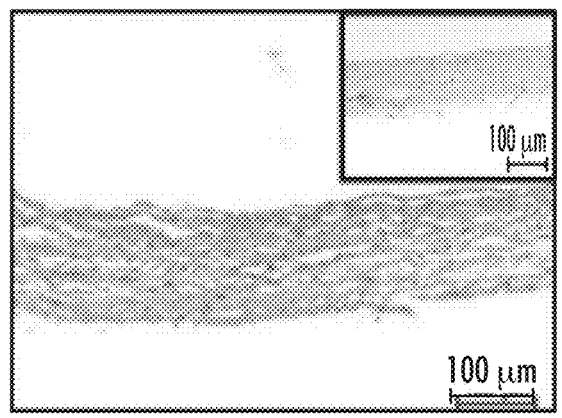
FIG. 6 is a histological image of fresh porcine pericardium demonstrating positive IHC staining for alpha-gal epitope (insert—negative IHC control).
Figure 7:
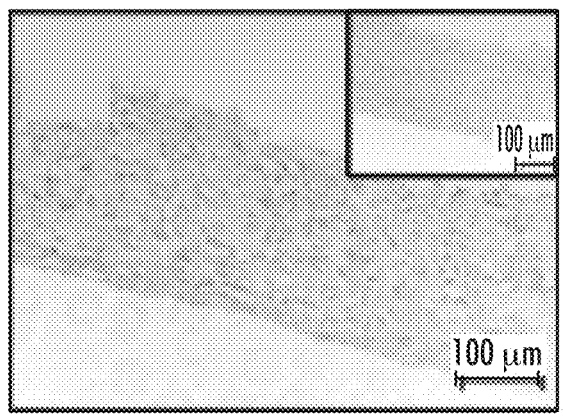
FIG. 7 is a histological image of decellularized porcine pericardium demonstrating positive IHC staining for alpha-gal epitope (insert—negative IHC control).

Histology results indicated the complete absence of intact porcine cell nuclei in decellularized samples with some evidence of tissue swelling and minor matrix disruption indicated by an increase in overall tissue thickness as compared to fresh pericardium (~150 µm) (see FIG. 4, showing fresh H&E stained pericardium and FIG. 5 showing decellularized H&E stained pericardium). The measured thickness of the decellularized pericardium ranged between 0.3-0.7 mm. Staining with 4',6-diamidino-2-phenylindole (DAPI) for cell nuclei was absent (data not shown). Additionally, IHC for alpha-gal, the xenogenic epitope responsible for acute rejection of porcine-derived materials in humans was present in fresh pericardium (FIG. 6) and absent in decellularized pericardium (FIG. 7).

Figure 8:
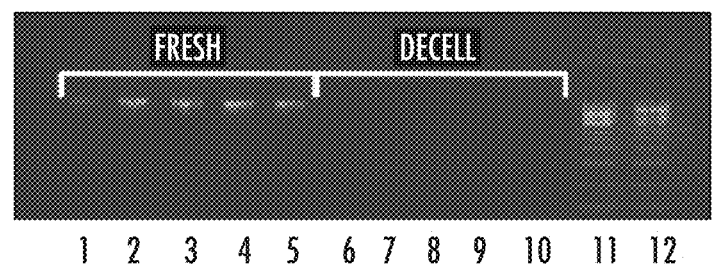
FIG. 8 illustrates ethidium bromide stained agarose gels for DNA isolated from fresh (lanes 1-5) and decellularized (lanes 6-10) pericardium (white bands=presence of DNA). A 300-24000 bp DNA standard ladder (lanes 11-12) is shown for comparison.
Figure 9:
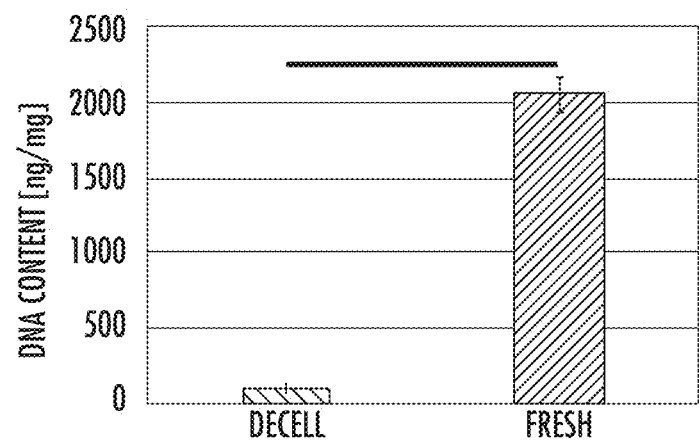
FIG. 9 illustrates DNA quantification of fresh and decellularized pericardium performed with Nanodrop spectrophotometry.

One percent agarose gels stained with ethidium bromide (FIG. 8) demonstrated the absence of residual DNA greater than 300 base pairs (bp), concomitant with a significant (p<0.05) 95% reduction in double stranded DNA content in decellularized pericardium compared to fresh tissue as determined by spectrophotometry (96.2±13.4 and 2051±112.7 ng/mg dry weight, respectively) (FIG. 9). These results are in alignment with Gilbert et al. and Crapo et al. that provide initial benchmarks defining minimal criteria for effective tissue decellularization (Gilbert, Freund, and Badylak 2009; Crapo, Gilbert, and Badylak 2011).

Figure 10:
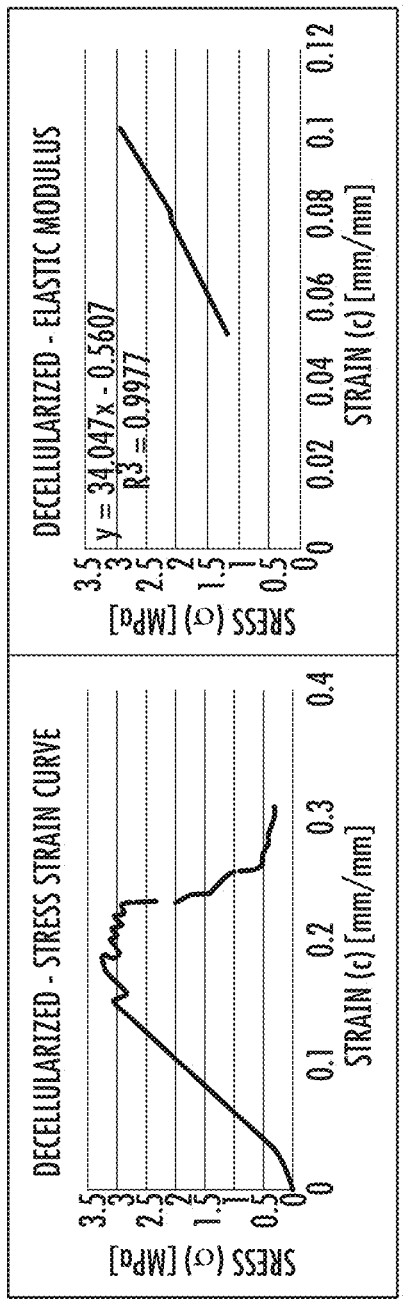
FIG. 10 includes a stress-strain plot (left) and an expanded view of the linear region of the modulus plot (right) as determined for decellularized porcine pericardium.

Modulus was calculated according to E=σ/ε, where a and c is the calculated engineering stress and strain, respectively. The modulus was determined from the linear region of the stress-strain curves between 0.05-0.1 (mm/mm) as performed by others. Statistical analysis was performed using Student's two-tailed t-test. Significance was defined as p<0.05. FIG. 10 graphically illustrates the stress/strain curve (left) and the linear region of the curve (right) for the decellularized pericardium. No significant differences were found for the average linear region modulus of decellularized and fresh pericardium (20.59±12.04 MPa and 16.97±9.57 MPa, respectively).

Figure 11:
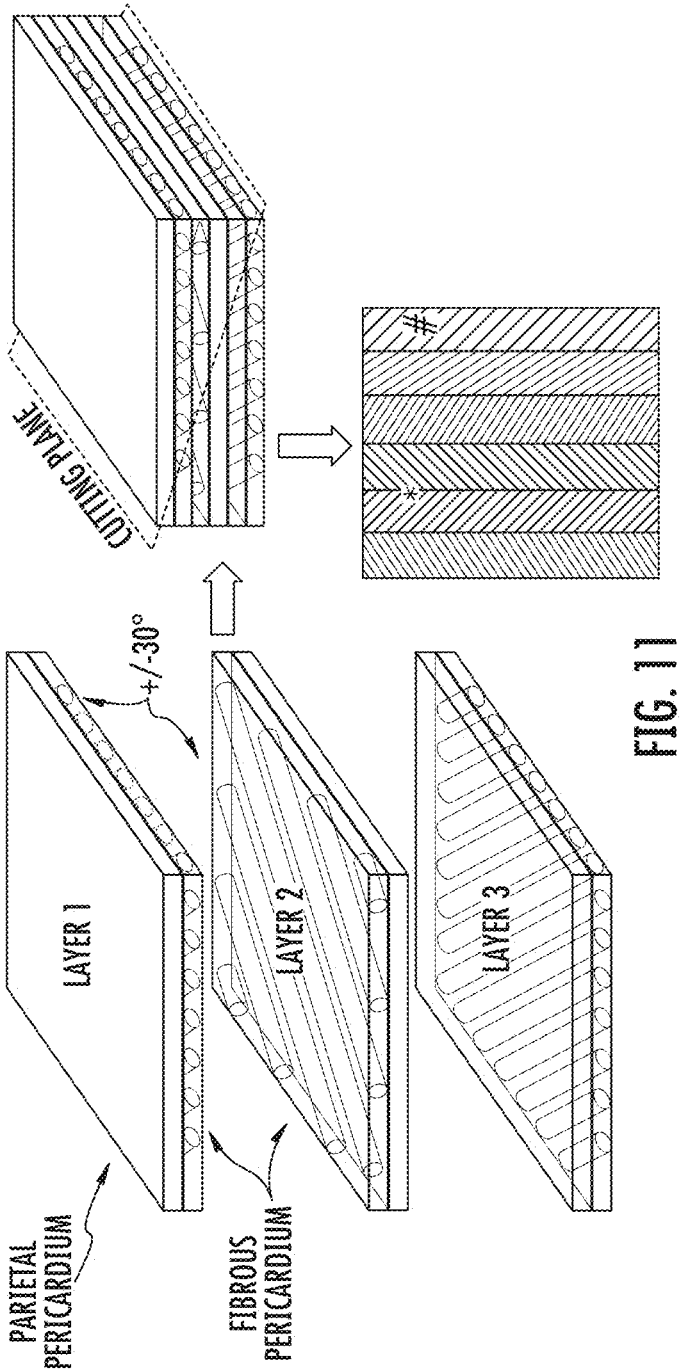
FIG. 11 includes a diagrammatic representation of multi-layer construct formation in which three plies of decellularized pericardium are stacked (cylinders represent aligned collagen type I fibers in the fibrous pericardium layer of each ply) oriented at ±30° to a common horizontal.
Figure 13:
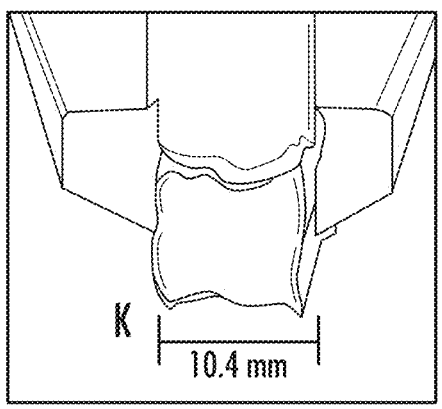
FIG. 13 is a macroscopic image of a 6-ply construct sewn with suture (black outline).

As illustrated in FIG. 11, to form multi-layer constructs, decellularized pericardium sheets were gently dried with tissue paper and sections of the tissue with a clearly defined collagen fiber aligned direction were identified in the fibrous pericardium and cut out into squares. The fiber aligned direction of each square was then oriented ±30° (verified via a protractor) relative to a stationary grid containing a common horizontal axis. Once aligned, sections were stacked and the multi-layer sheets were placed upon a dissolvable embroidery backing material, which allowed for easy positioning within a sewing machine and enabled sewing needle penetration through all pericardium layers. A square pattern was sewn around the periphery of the sheets followed by removal of excess tissue and backing material (FIG. 13). The constructs, along with the backing were soaked in saline for 30 minutes to ensure that the backing had completely dissolved.

Figure 12:
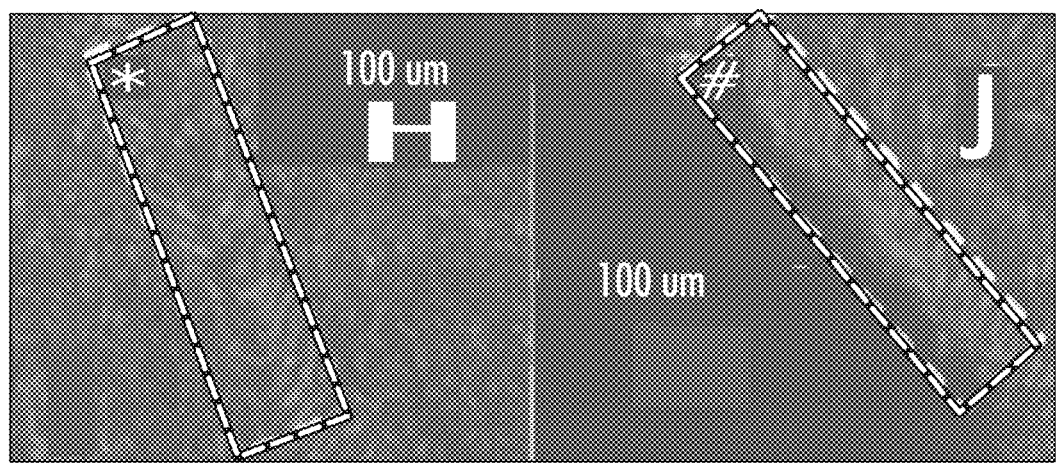
FIG. 12 illustrates chevron pattern (left panel) and half chevron pattern (right panel) in the dashed white outlines that were observed within different areas of a formed construct via polarized light microscopy confirming the presence of oriented collagen fiber alignment, (total magnification: 100×).

To illustrate that constructs could be made with adjacent plies having an aligned collagen fiber-preferred direction oriented at ±30° relative to a common horizontal, polarized light microscopy was performed in conjunction with employing a red fluorescence wavelength filter to visualize multi-layer patches that had been sectioned obliquely across the sample in order to observe multiple layers (FIG. 11). Histological inspection of patch sections illustrated the presence of "chevrons" (FIG. 12) indicating the location at which the collagen directions in immediately adjacent layers of fibrous pericardium intersect at opposing ±30° angles to the common horizontal.

Mechanical evaluations were carried out on 10 mm×10 mm multi-layer constructs (FIG. 13) consisting of from one to six sheets (or plies), which ranged in total thickness of 0.25-1.60 mm, respectively. The native annulus fibrosus is subject to complex stretching and loading including biaxial strains and circumferentially directed tensile hoop stresses developed due to spinal motions and interdigenerated by the nucleus pulposus. As such it is important to assess the inherent strength of the construct biomaterials to resist biaxial burst.

Figure 14A:
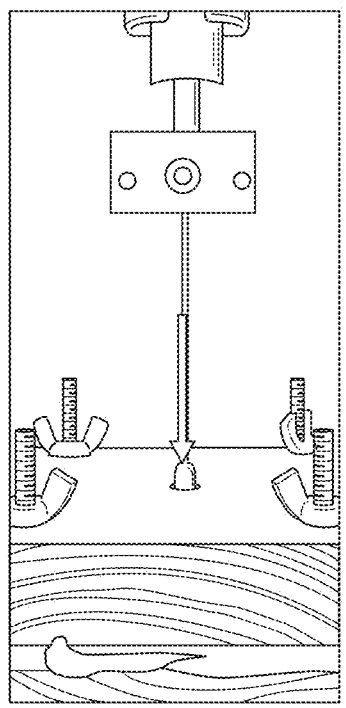
FIG. 14 illustrates at panel A a testing mechanism for examination of biaxial impact strength. Panel B schematically illustrates a testing protocol. Panel C is a graph showing burst strength of a 2-layer AF patch withstanding ~160N load force during testing.
Figure 14B:
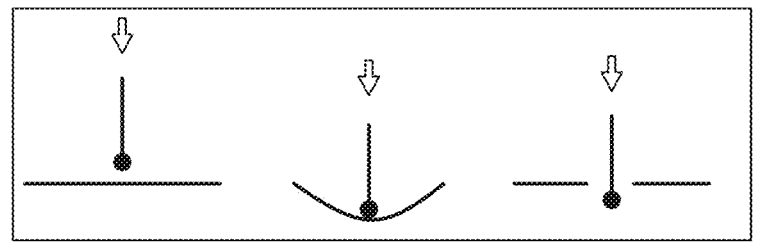
Figure 14C:
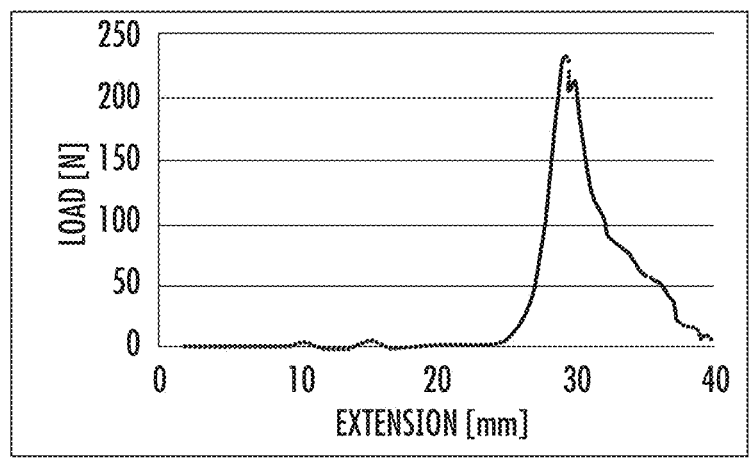

Single layers of decellularized pericardium and constructs of 2-, 3-, and 6-ply (n=6 each) were assembled and subjected to biaxial ball burst directed radially (perpendicular to axis of the patch fibers) so as to generate/simulating a potential large herniation or expulsion of a nucleus pulposus replacement through the patch thickness. Briefly, constructs were placed in a custom designed stationary test fixture (FIG. 14, panel A), which centered and secured the construct between two restraining blocks lined with course grit sandpaper and containing a 6.25 mm diameter thru hole. The fixture and patches were secured to the base of an Instron mechanical test frame fitted with a 1000N load cell. A 6 mm diameter stainless steel ball was welded to a push rod, which was secured to the test frame crosshead. The crosshead was lowered such that the rod and ball were directed into the thru hole of the stationary test fixture until contact was made with the secured constructs (indicated by the generation of a 0.1N preload) (FIG. 14, panel B). Testing was performed at a rate of 300 mm/m in in accordance with ASTM D3786/M—Standard test method for bursting strength of textile fabrics (ASTM 2002), until patch rupture. The resultant ball-burst pressure at failure was calculated given the maximum force at rupture (FIG. 14, panel C) and its relationship with ball-burst pressure according to established equations (Equations 1-3) given the geometric constraints of the test set-up.

$$P = \frac{P}{A} = \frac{F}{(2\pi d^2(1-\cos(\varphi))} \quad \text{Equation 1}$$

$$\varphi = \pi - \left(\frac{\pi}{2} - \tan^{-1}\left(\frac{d}{f}\right)\right) - \tan^{-1}\frac{a}{b} \quad \text{Equation 2}$$

$$f = \sqrt{(b^2 + a^2 - d^2)} \quad \text{Equation 3}$$

in which:
P is the ball burst pressure,
F is the maximum recorded burst force,
A is the contact area between the construct and the surface of the steel ball,
φ is the contact angle between the construct and ball,
d is the radius of the steel ball,
f is the magnitude of the vector representing the stretching material that is geometrically determined from:
a; the distance between the central axis of the ball and tissue clamp set-up (3.25 mm),
b; the position of the steel ball and push rod relative to its starting point (3 mm) that maintains the tangential relationship between the patch material and surface of the ball.

Figure 15:
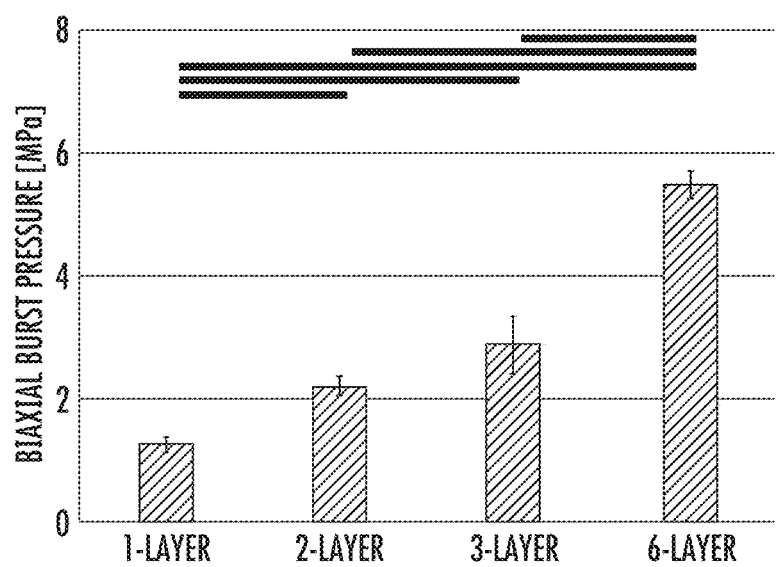
FIG. 15 presents a graph of the average maximum biaxial burst strength of 1-, 2-, 3-, and 6-ply constructs. Solid lines connecting different groups on the graph indicate a significant difference (p<0.05).

Burst strength results illustrated a positive correlation between the number of layers used in patch construction and burst pressure (FIG. 15). Constructs of 1-, 2-, 3-, and 6-ply exhibited average biaxial burst strengths of 1.28±0.12 MPa, 2.25±0.16 MPa, 2.92±0.46 MPa and 5.53±0.23 MPa, respectively (FIG. 15). All values were significantly different from each other (p<0.05) except between 2- and 3-ply constructs. The three-ply material exhibited biaxial burst strengths exceeding the highest reported in vivo intravertebral disc pressure value of 2.3 MPa measured in human lumbar intervertebral discs when lifting a 20 kg load with flexed back (dotted line, FIG. 14, panel D) while maintaining a significant safety factor.

Figure 16:
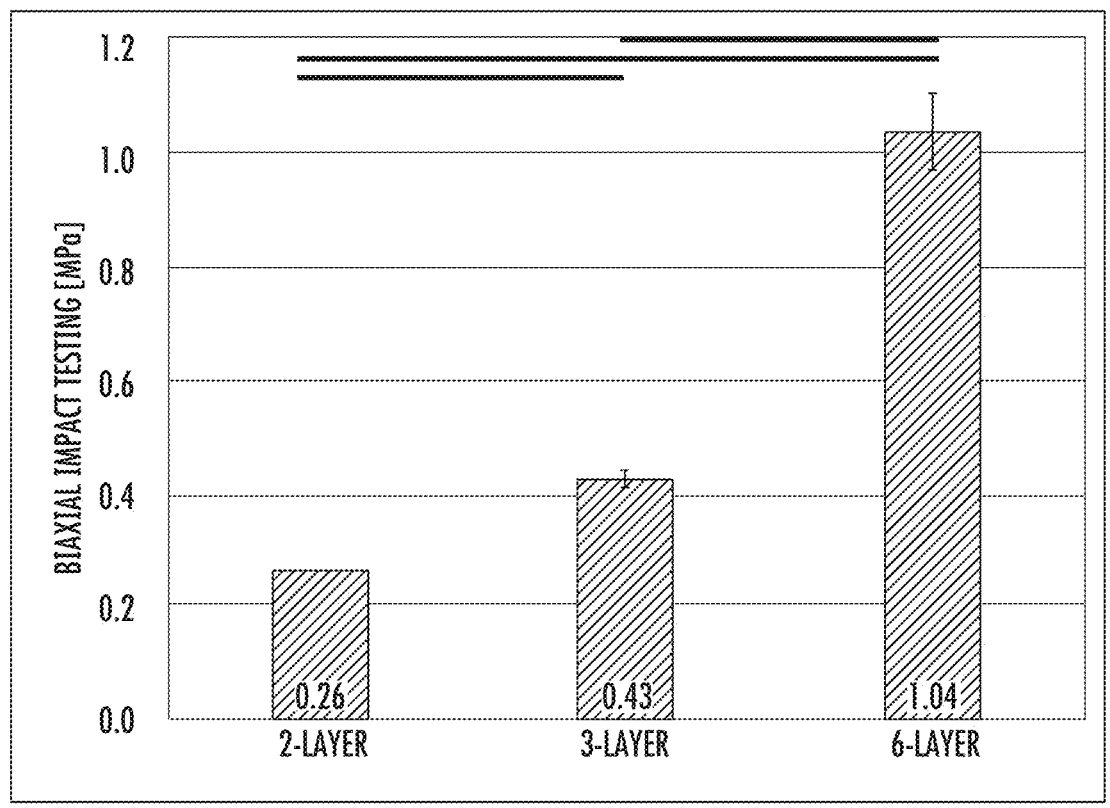
FIG. 16 is a graph of the average maximum calculated biaxial impact pressure withstood by 2-, 3-, and 6-layer AF patches. Solid lines connecting different groups on graph indicate a significant difference (p<0.05).

Biaxial Impact Strength was modeled after ASTM D1709 with minor modification. A custom design impact weight sled fixture was developed to determine the maximum impact load withstood by 2-, 3- and 6-layer AF patches (n=4 per group). Briefly, increasing weights, ranging from 0.18-0.58 kg, were dropped from a constant height of 0.254 meters in order to calculate and determine the impact force and maximum impact strength. Impact strength was analytically determined using a ball-burst test with equations as described above. Results are shown in FIG. 16.

Uniaxial tensile testing was performed on 3-ply constructs (n=6) according to methods described in the art. Briefly, patches were affixed between two tensile grips such that the fiber alignment of the patches was oriented ±30° to the axis of applied tension. Additionally single layer (SL) sheets of pericardium (n=6) were tested in the fiber-preferred (tensile loading applied in the direction of collagen fiber alignment) and cross-fiber (tensile load applied perpendicular to collagen fiber alignment) directions. The testing protocol consisted of applying 5 preconditioning cycles to 10% strain followed by testing to failure at a rate of 240 mm/m in.

Figure 17:
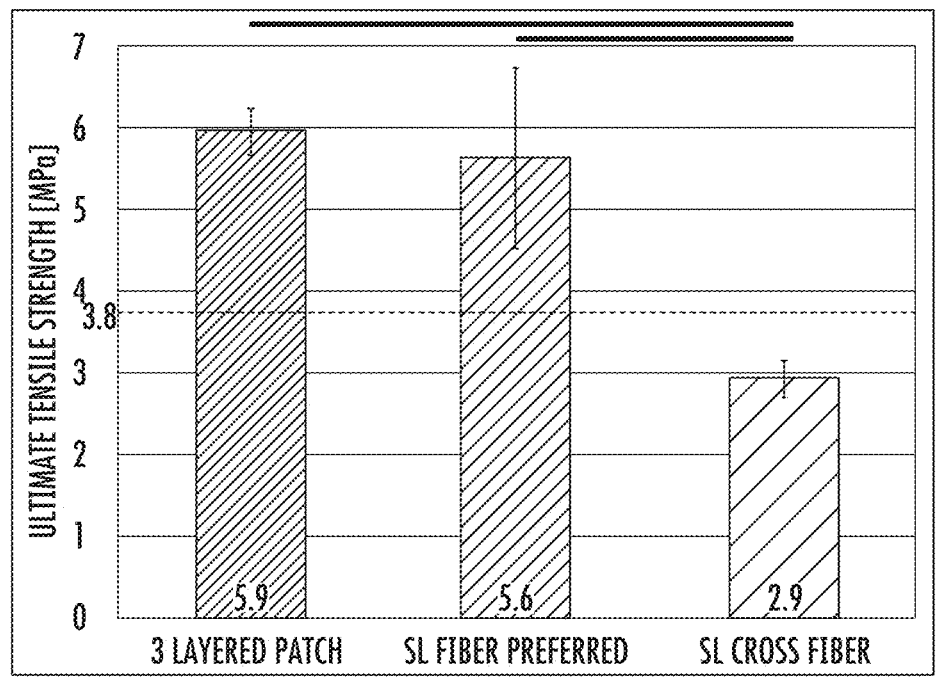
FIG. 17 is a graph illustrating the average ultimate tensile strength of 3-layer constructs and single layer sheets aligned in fiber preferred and cross fiber directions (Dotted horizontal line indicates measured posterior human annulus fibrosus ultimate tensile strength (3.8 MPa). The solid lines connecting different study groups on the graph indicate a significant difference (p<0.05).

The average ultimate tensile strength (UTS) of the 3-ply construct and the single layer decellularized pericardium in the fiber-preferred and cross-fiber directions were 5.9±0.3 MPa, 5.6±1.1 MPa and 2.9±0.2 MPa, respectively (FIG. 17). The UTS of the single-ply pericardium tested in the cross-fiber direction was significantly different (p<0.05) from the single-ply sampled tested in the fiber-preferred direction as well as the multi-layer construct.

Figure 18:
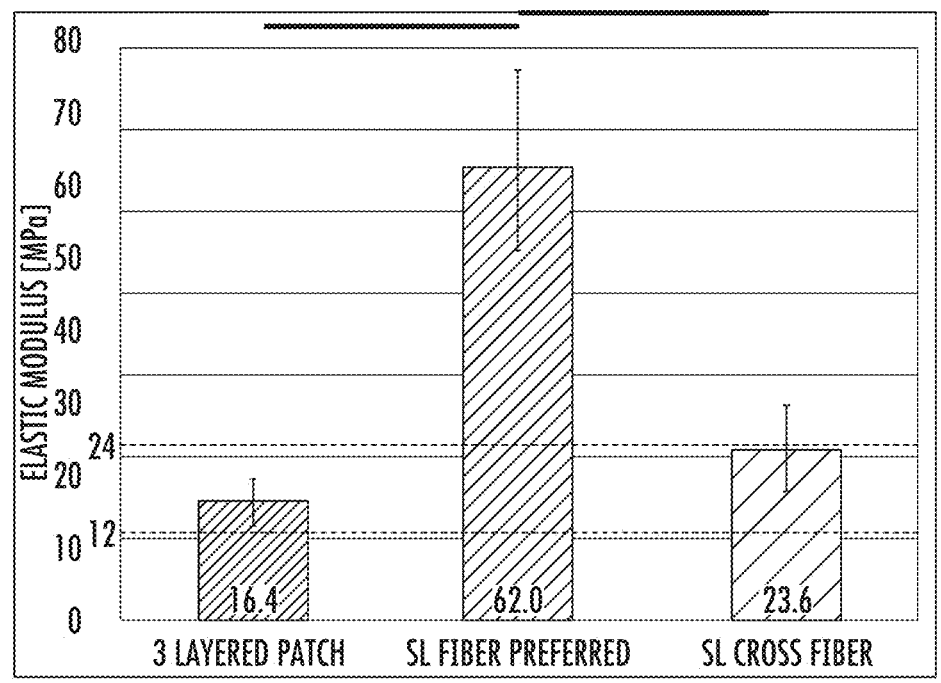
FIG. 18 is a representative graph illustrating the average elastic modulus of 3-layer construct and single layer sheets aligned in fiber preferred and cross fiber directions (Dotted horizontal lines indicate measured posterior human annulus fibrosus elastic modulus (12-24 MPa). The solid lines connecting different study groups on the graph indicate a significant difference (p<0.05).

Modulus values were determined from the linear region of the resultant stress strain curves. Stress strain curves demonstrated a non-linear profile as is reminiscent of a viscoelastic material. Average linear circumferential modulus of the 3-ply construct, single-ply decellularized pericardium tested in the fiber-preferred and cross-fiber directions were 16.4±3.5 MPa, 62.0±13.6 MPa and 23.6±6.0 MPa, respectively (FIG. 18).

Overall, the UTS and modulus values of the 3-ply constructs mirror the values reported for posterolateral human annulus fibrosus tissue (3.8±1.9 MPa, and 12-24 MPa, respectively). Furthermore, the average linear modulus of a single sheet of decellularized pericardium in the fiber preferred direction matched values reported for single AF lamellae from the outer AF (64.8 MPa).

Figure 19:
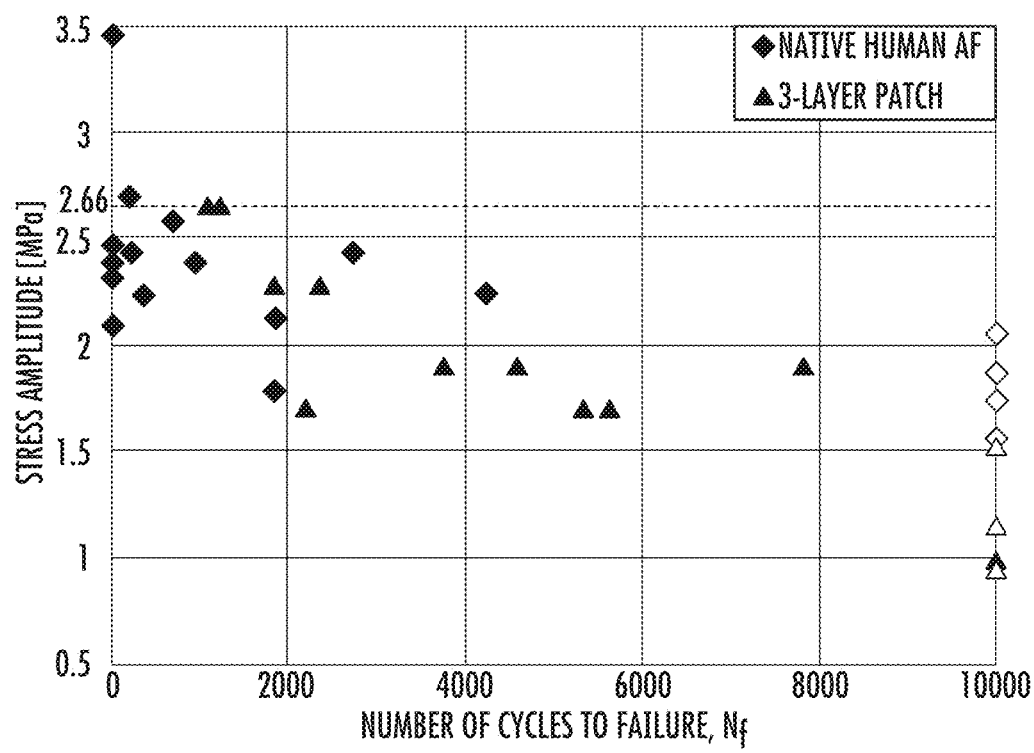
FIG. 19 presents fatigue strength of 3-layer constructs in comparison to native human annulus fibrosus (Dotted horizontal line indicates 70% ultimate tensile strength of measured human annulus fibrosus (the maximum stress observed due to prevention of injury by the neural arch)). Open diamonds and triangles indicate specimens with no mechanical failure observed (following mechanical run out to 10,000 cycles).

Tensile Fatigue Testing of 3-layered constructs was performed using a Bose ElectroForce test frame fitted with a saline bath at 25° C. 3-layer constructs (n=10) were oriented and preconditioned as previously described for tensile testing, and fatigued to a maximum of 10,000 cycles over a range of stress amplitudes to develop an S-N curve as illustrated in FIG. 19.

Table 1, below summarizes several of the average maximum calculated mechanical characteristics for 3-layer constructs and compares those values to reported literature values of native human annulus fibrosus tissue.

TABLE 1

| Test | 3-layer construct | Human annulus fibrosus tissue |
| --- | --- | --- |
| UTS | 5.9 ± 0.3 MPa | 3.8 MPa |
| Elastic modulus | 16.4 ± 3.5 MPa | 12-24 MPa |
| Tensile strain at break | 69.92 ± 6.44% | 50-65% |

TABLE 1-continued

| Test | 3-layer construct | Human annulus fibrosus tissue |
| --- | --- | --- |
| Burst | 2.92 ± 0.46 MPa | 0.1-2.3 MPa |
| Impact | 0.43 ± 0.02 MPa | 0.1-2.3 MPa |
| Tensile fatigue (70% UTS) | 1155 cycles | 448 cycles |
| Tensile fatigue (endurance limit) | 1.52 MPa | 2.05 MPa |

EXAMPLE 2

Cytocompatibility of multi-layer constructs formed as described in Example 1 was assessed after seeding patches with bovine caudal intervertebral disc annulus fibrosus cells. Briefly, cow tails were collected within two hours of slaughter and caudal intervertebral discs were isolated via blunt dissection. Annulus fibrosus tissue was minced into 2-4 mm² pieces and digested in DMEM containing 0.2% collagenase (Type I-125U/mg) and 1% antibiotic/antimycotic (Ab/Am) for 18 hours at 37° C.

Prior to seeding, multi-layer constructs were sterilized using 0.1% peracetic acid in phosphate buffered saline solution (pH 7.5) for 2 hours at room temperature prior to thorough rinsing in sterile saline and overnight neutralization in a solution of 48% FBS, 50% DMEM and 2% Ab/Am. Annulus fibrosus cells were seeded drop-wise in 75 μl of media containing $1 \times 10^5$ cells (passage 4) on to the surface of 10×10 mm constructs. Cells were allowed to attach for 3 hours prior to being flipped and seeded on the opposite surface. Additionally, following surface seeding, patches were injected with $1 \times 10^5$ between the layers using a 20G syringe. Cells were allowed to culture under standard conditions for up to 15 days.

Figure 20:
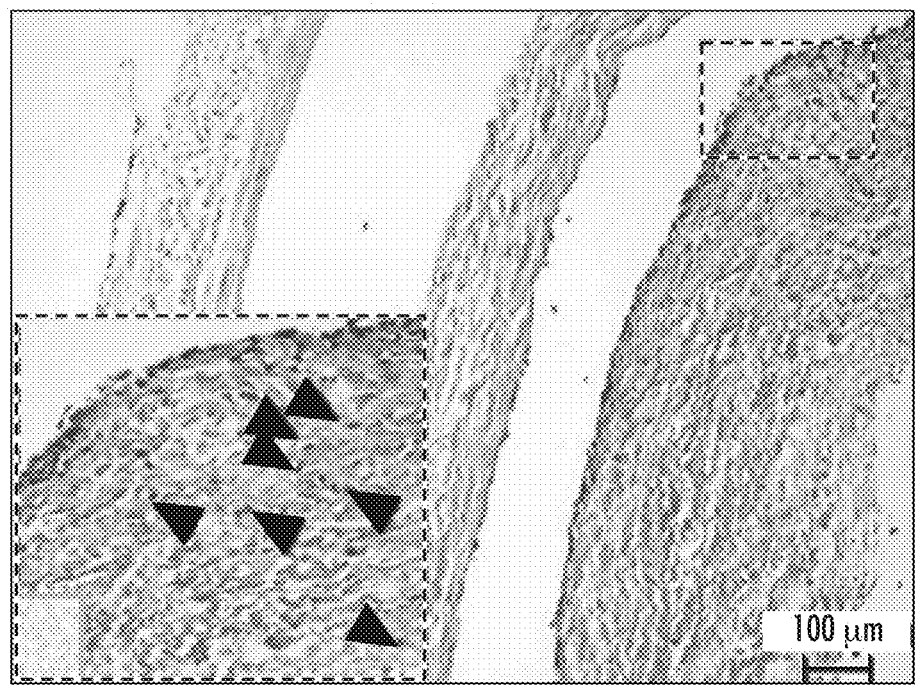
FIG. 20 illustrates a histological image of a 3-ply patch (with layers separated for clarity) illustrating the presence of annulus fibrosus cells on the surface and penetrating (insert, total magnification: 200×) the patch after 6 days of in vitro culture (total magnification: 50×). The arrow heads point to individual cells.

Histological analysis of cell-seeded patches (n=3/time-point) was completed on paraffin embedded, 5 μm sections stained with H&E, which were imaged on a Zeiss AxioVert A1 microscope with Axiovision software. Histological results confirmed annulus fibrosus cell attachment to the surfaces of the multi-layer patches forming a monolayer. Furthermore, there was evidence of cellular infiltration into the lamellae of the patches as well (FIG. 20).

DNA content and cell death on the patches was assessed via Picogreen (n=3 patches/time-point) and lactate dehydrogenase (LDH; n=3 patches/time-point) assays, respectively according to manufacturer's instructions. To determine the number of cells attached to the multi-layer constructs, a standard curve was developed from known numbers of bovine annular fibrosus cells seeded in well plates subjected to Picogreen analysis. Additionally, LDH values were expressed as a percentage of a positive cell death control developed by snap freezing cell-seeded constructs 3 days prior to LDH analysis on the culture media.

Figure 21:
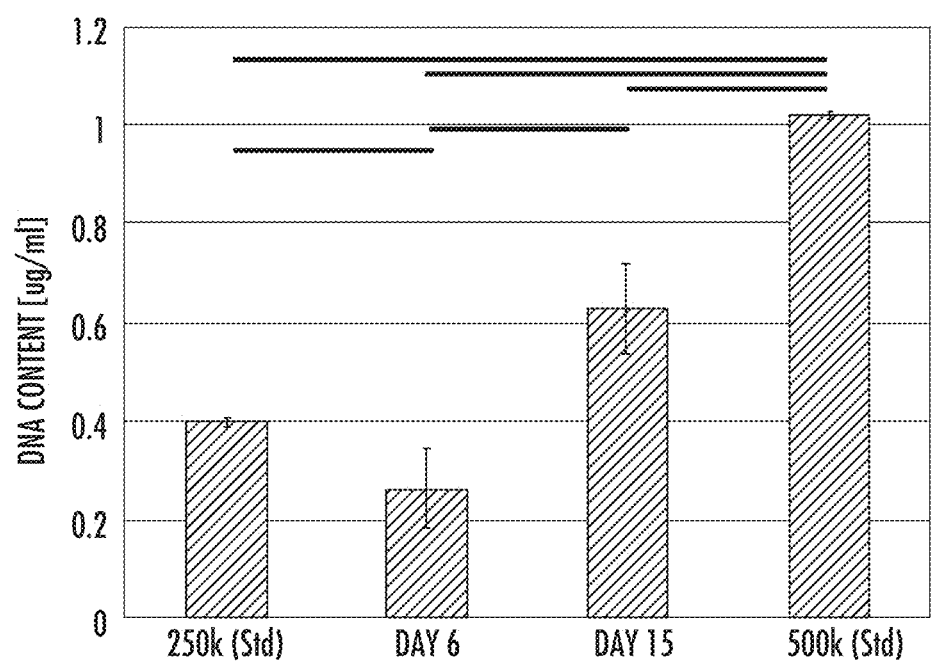
FIG. 21 is a graph illustrating bovine annulus fibrosus cell DNA content within 3-ply constructs following 6 and 15 days of culture as compared to a DNA standard curve generated from a known numbers of viable annulus fibrosus cells.

As seen in FIG. 21, DNA content of multi-layer constructs significantly (p<0.05) increased between day 6 and day 15 (0.264±0.081 and 0.625±0.090 μg DNA/ml, respectively) suggesting cell proliferation over time in culture. Interpolation from a standard curve developed from known numbers of bovine annular fibrosus cells demonstrated greater than $3 \times 10^5$ cells on each patch by day 15.

Figure 22:
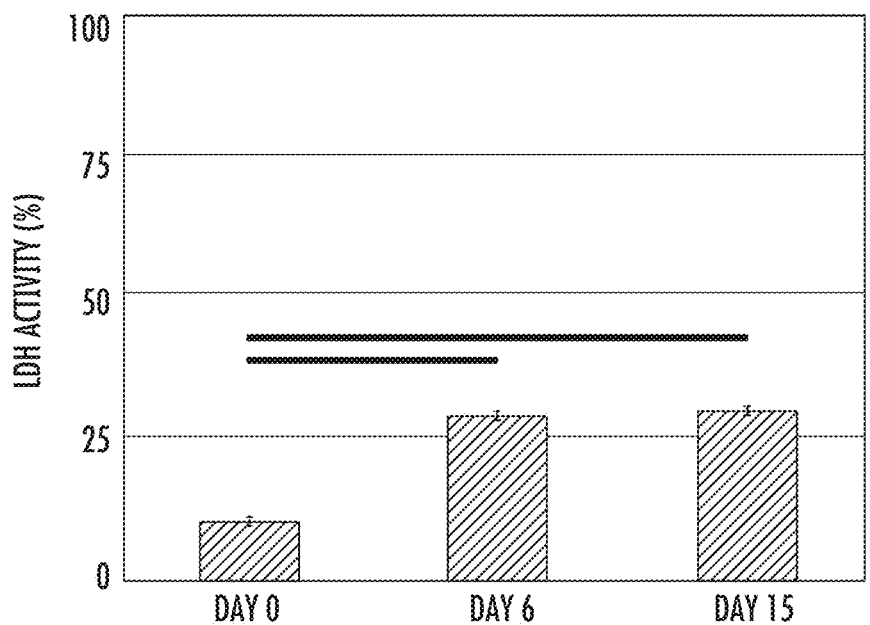
FIG. 22 is a graph illustrating percent lactate dehydrogenase produced by bovine annulus fibrosus cell seeded 3-ply patches immediately following seeding (Day 0) and after 6 and 15 days of culture relative to a positive cell death control (i.e. annulus fibrosus cell seeded 3-ply patches subjected to snap freezing with liquid nitrogen to induce 100% cell death). Solid lines connecting different study groups on graphs indicate a significant difference (p<0.05).
Figure 23:
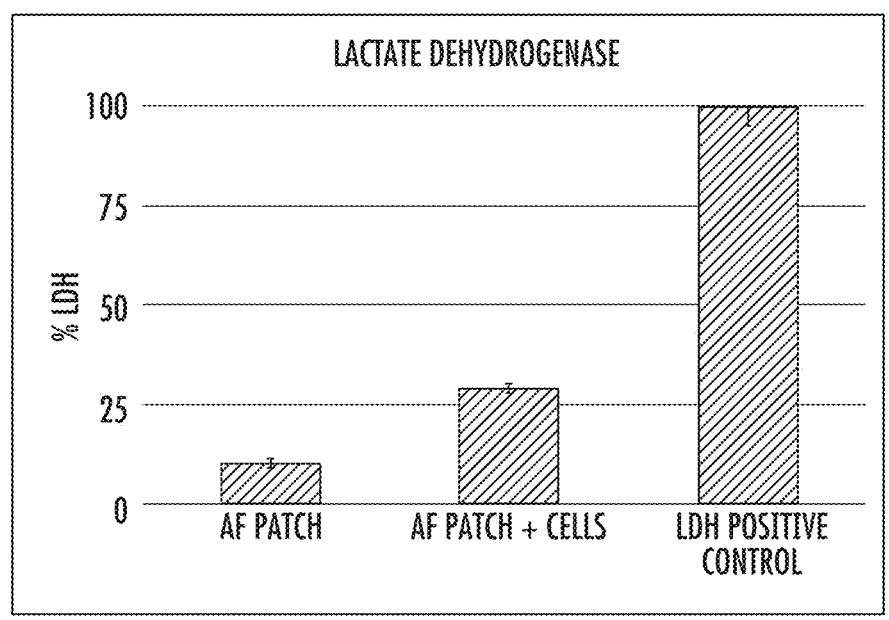
FIG. 23 compares the average lactate dehydrogenase (LDH) content on Day 6 for a construct, a cell seeded construct, and a positive control.

LDH content of culture media surrounding patches immediately following seeding (day 0) and after 6 and 15 days of culture was 10.31±0.48%, 28.72±1.22% and 29.94±0.90%, respectively as compared to positive controls at each respective time-point (FIG. 22). While LDH values at day 6 and 15 were both significantly different (p<0.05) compared to day 0, there was no difference between days 6 and 15 indicating that there was no increase in cell death with increasing time in culture therefore illustrating cytocompatibility of multi-layer constructs. FIG. 23 graphically compares the LDH values at day 15 for the cell-seeded constructs, constructs with no seeded cells, and an LDH positive control.

EXAMPLE 3

Chemical crosslinking solutions were used to examine the effects of enzymatic degradation on multi-layer constructs. Briefly, 3-layer constructs formed as described above were treated with cross-linking formulations as follows:

EDC: 6 mM or 30 mM 1-Ethyl-3-(3-dimethylaminopropyl) Carbodiimide HCL (EDC) and 1.2 or 6 mM N-Hydroxysuccinimide (NHS), respectively, buffered in 50 mM MES at (pH 5.5) at ambient temperature for 24 hours.

GLUT: 0.2% or 0.6% glutaraldehyde in 50 mM 4-(2-hydroxyetheyl)-1-piperazineethanesulfonic acid (HEPES) buffered saline (pH 7.4) at ambient temperature for 24 hours.

Resistance to thermal denaturation temperatures (Td) were measured in native bovine annulus fibrosus samples, control constructs (no crosslinking), and constructs fixed with EDC (6 mM and 30 mM) and GLUT (0.2% and 0.6%) to determine collagen crosslinking stability. Briefly, differential scanning calorimetry (DSC) (Model DSC Q1000, TA Instruments, Newcastle, Del.) was used to determine $T_d$ (n=3 samples/per fresh, decellularized patches, and native bovine AF groups) (n=4 samples per crosslinked groups). Heating of each sample was performed at a rate of 10° C./minute from 20 to 120° C. The denaturation temperature was recorded as the maximum value of the endotherm peak.

Figure 24:
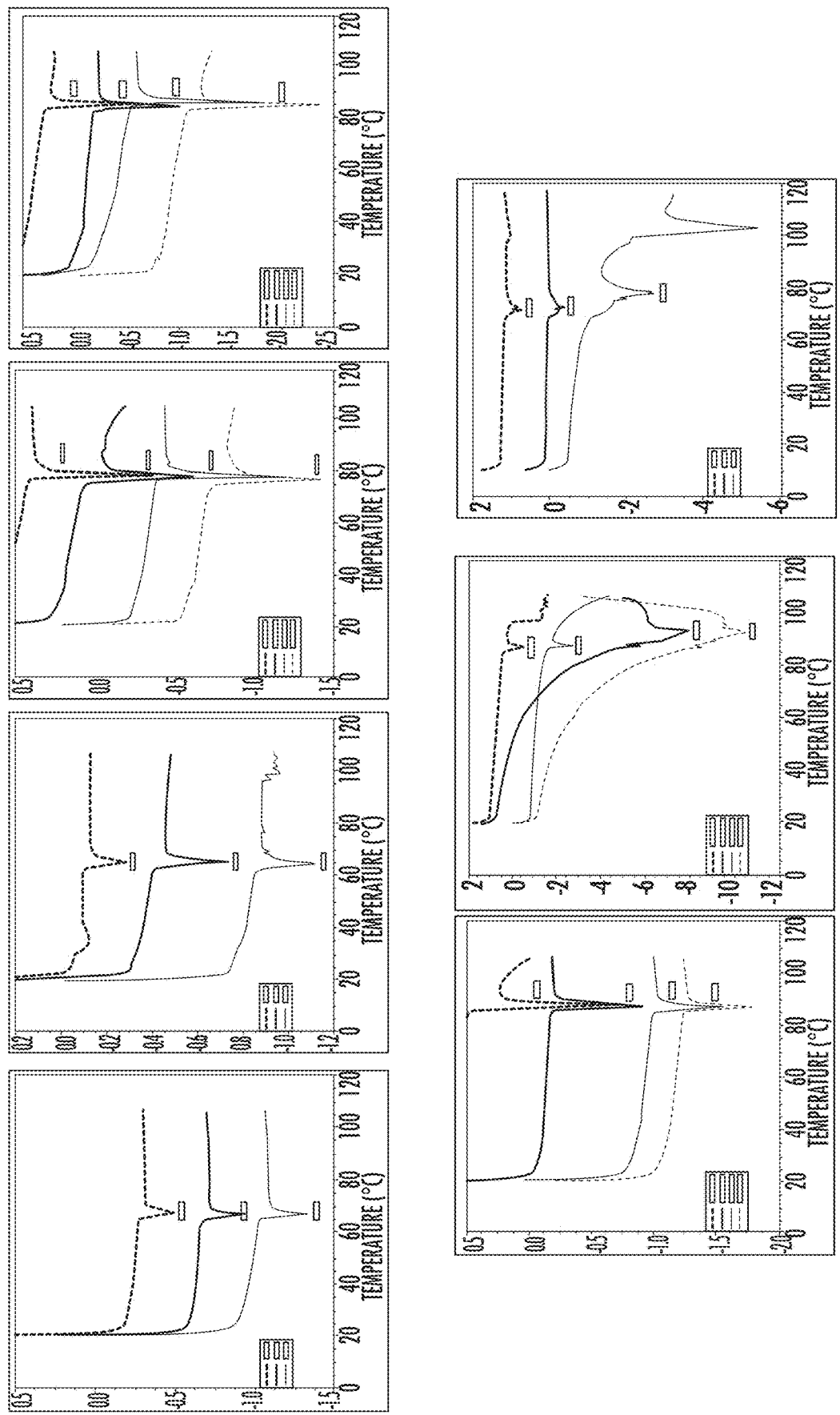
FIG. 24 illustrates differential scanning calorimetry results of denaturation temperature of A) fresh pericardium, B) decellularized porcine pericardium, C) construct crosslinked with EDC (6 mM), D) construct crosslinked with EDC (30 mM), E) construct crosslinked with 0.2% glutaradehyde, F) construct crosslinked with 0.6% glutaraldehyde, and G) native annulus fibrosus.

Results are shown in FIG. 24 including
panel A—fresh pericardium,
panel B—decellularized porcine pericardium,
panel C—construct crosslinked with EDC (6 mM),
panel D—construct crosslinked with EDC (30 mM),
panel E—construct crosslinked with 0.2% glutaradehyde
panel F—construct crosslinked with 0.6% glutaraldehyde,
and G) native annulus fibrosus Table 2, below, presents the average denaturation temperature for each sample.

TABLE 2

| Sample | Average $T_d$ (° C.) | Standard Error of the Mean |
|---|---|---|
| Fresh | 67.22 | 0.14 |
| Decellularized | 64.86 | 0.29 |
| EDC (6 mM) | 78.66 | 0.31 |
| EDC (30 mM) | 86.00 | 0.37 |
| GLUT (0.2%) | 87.50 | 0.26 |
| GLUT (0.6%) | 90.28 | 2.00 |
| Native tissue | 73.61 | 1.93 |

Figure 25:
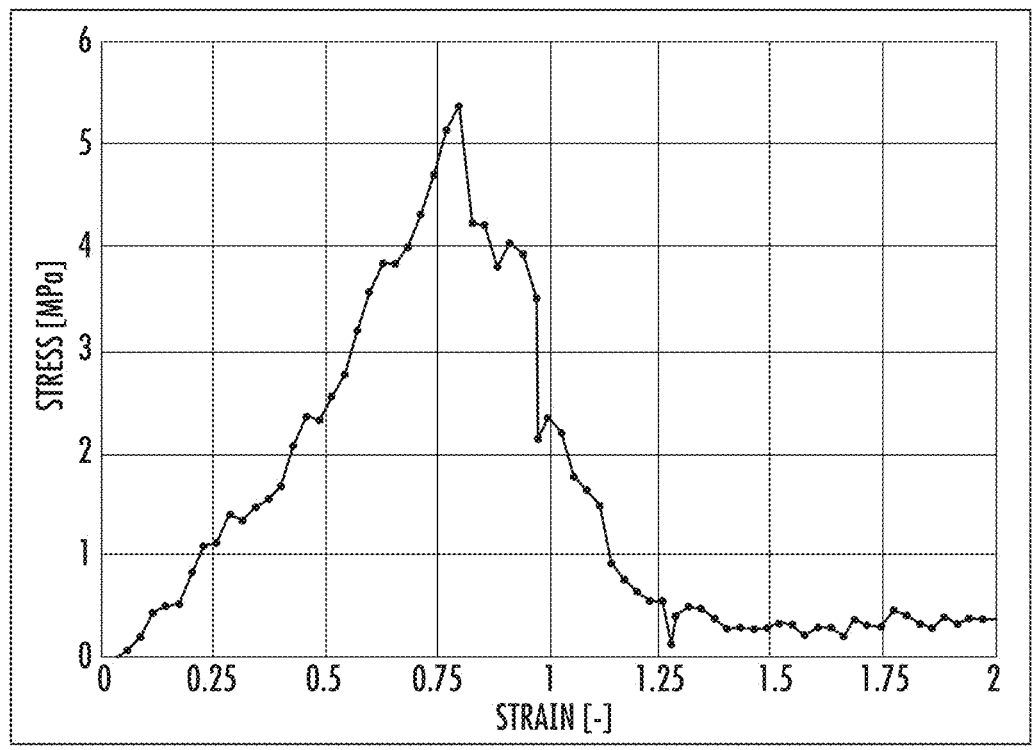
FIG. 25 presents a graph of the stress strain curve for tensile testing of a glutaraldehyde crosslinked 3-layer construct.
Figure 26:
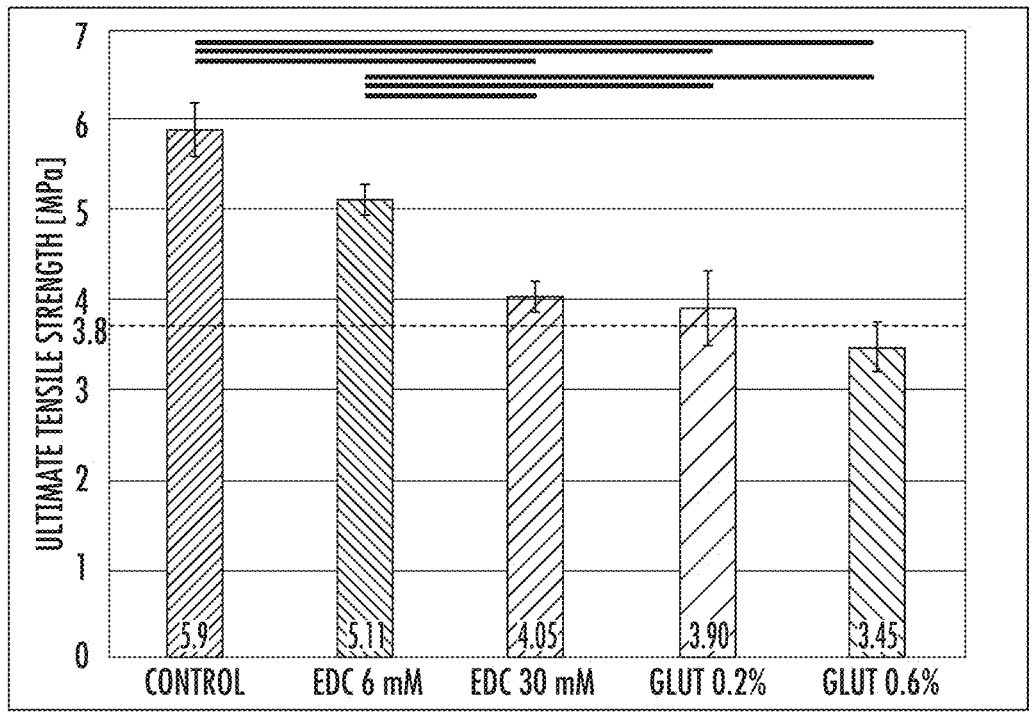
FIG. 26 graphically illustrates the overall ultimate tensile strength of constructs as disclosed herein.
Figure 27:
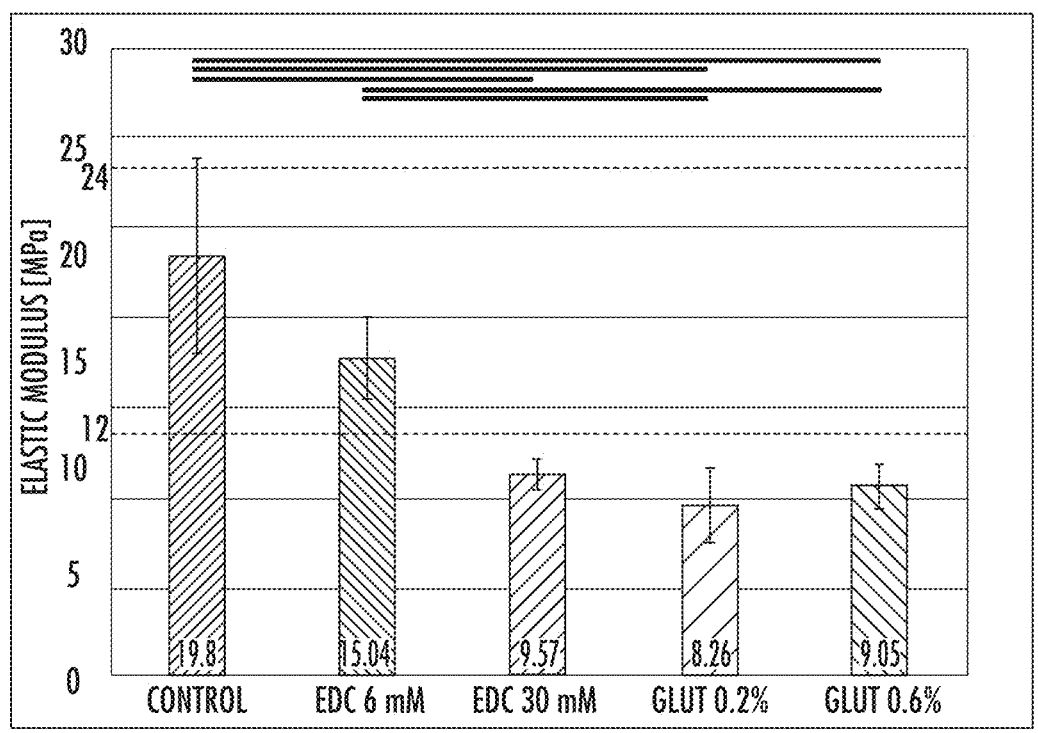
FIG. 27 graphically illustrates the elastic modulus obtained for multi-layered constructs as disclosed herein.

Ultimate Tensile Strength (UTS) of 3-layered constructs was determined using tensile testing according to methods described in the art. Briefly, 3-layer constructs including a non-crosslinked control sample and constructs crosslinked as described above were tested (n=5/per group). Preconditioning was performed (5 cycles to 10% strain at 10 mm/min) on an Instron mechanical system, followed by testing to failure at a rate of 240 mm/min to determine ultimate tensile strength (UTS) and strain at break. Elastic modulus (EM) was determined within the linear region of the stress-strain curve. FIG. 25 illustrates the stress strain curve obtained for the 0.6% glutaraldehyde crosslinked sample. FIG. 26 illustrates the overall UTS of the different samples. As shown, the crosslinked constructs exhibited a loss in UTS as compared to the control. FIG. 27 illustrates the comparison of elastic modulus of the different samples. As can be seen, the crosslinking of the constructs led to a loss in elastic modulus as the non-crosslinked construct exhibited a higher elastic modulus. For comparison, the typical range for human annulus fibrosus elastic modulus is denoted on the figure by the black dotted lines.

To determine resistance to collagenase degradation of the different test samples, control and crosslinked 3-layered constructs as well as native bovine annulus fibrosus (n=3/per group) were rinsed in TRIS buffer, blotted dry, frozen, lyophilized, and weighed. Samples were then incubated in 2 mL of 33.6 U/mL collagenase type I (Worthington—MX1D12644: 300 U/mg) buffered in 50 mM TRIS, 10 mM calcium chloride, pH 8.0 at 37° C. for up to 14 days (Days 1, 3, 7 and 14) while shaking at 250 RPM. Following, enzyme liquid was discarded and the samples were rinsed in TRIS buffer, blotted dry, frozen, lyophilized, and weighed. Average percent weight loss was then calculated.

Day 7 samples were extended due to minimal degradation of crosslinked samples. These samples were incubated in 2 mL of 336 U/mL collagenase type I (Worthington—MX1D12644: 300 U/mg) buffered in 50 mM TRIS, 10 mM calcium chloride, pH 8.0 at 37° C. for an additional 7 days.

Figure 28:
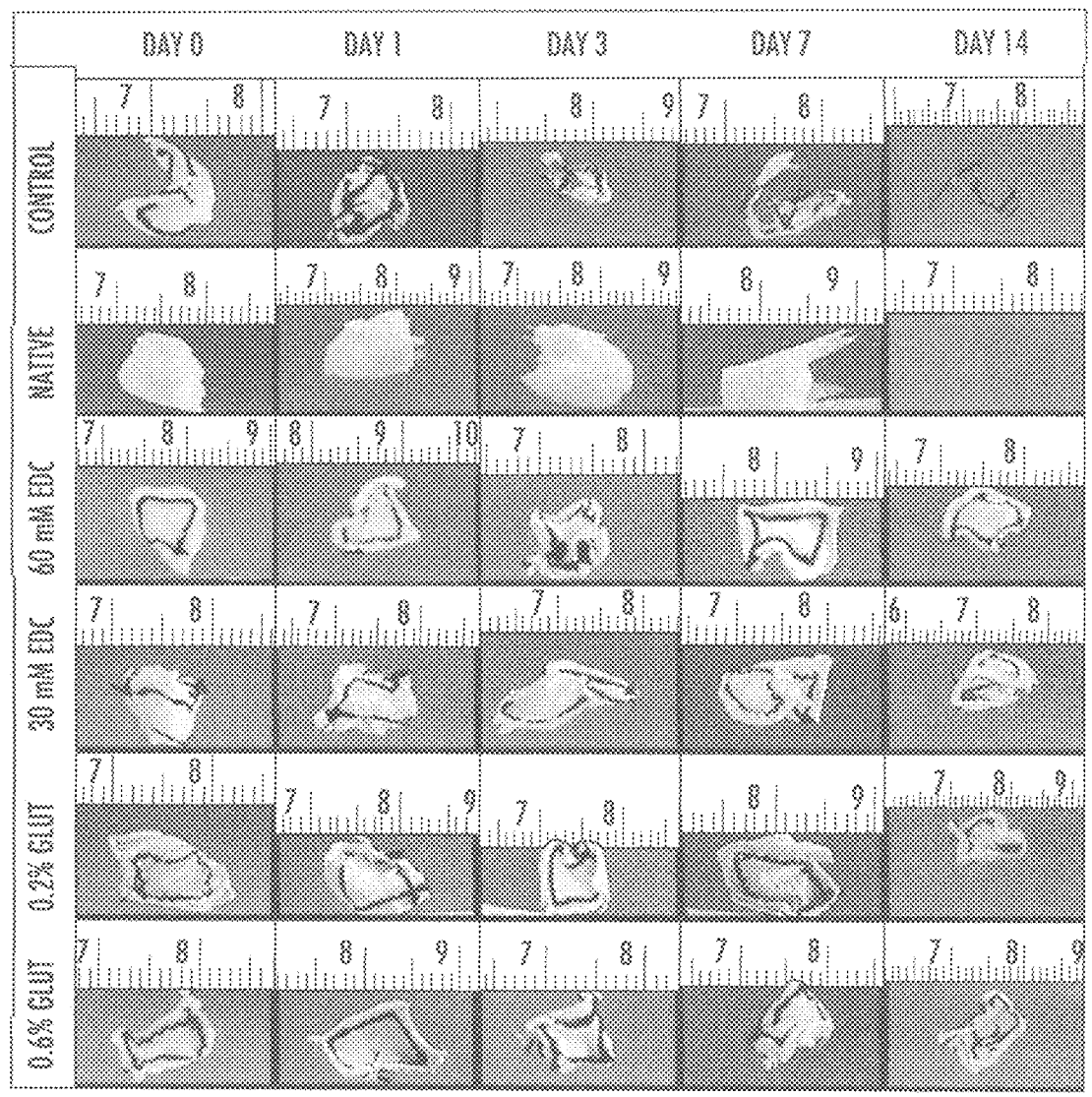
FIG. 28 illustrates the degradation over time for cross-linked and non-crosslinked multi-layer constructs.
Figure 29:
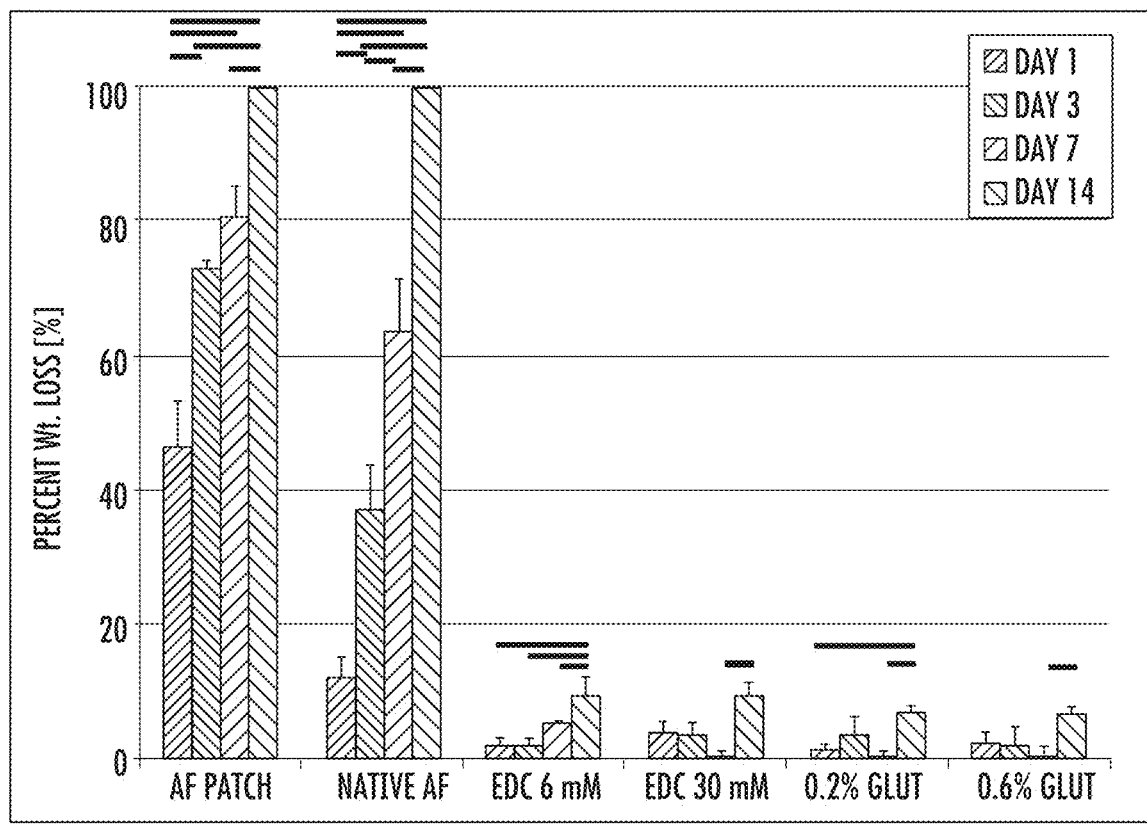
FIG. 29 graphically illustrates the percent mass loss indicating the levels of degradation over time for the constructs of FIG. 28.

FIG. 28 presents images of the different samples over the testing period. As can be seen, the native annulus fibrosus and the non-crosslinked control construct experienced 100% mass degradation, while the crosslinked constructs experienced a smaller degree of degradation. As shown in FIG. 29, the non-crosslinked control construct and the native annulus fibrosus material demonstrated and significantly greater percentage weight loss as compared to the crosslinked materials.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A biocompatible multi-laminate, angle-ply construct comprising:
a first sheet including a first decellularized tissue, the first decellularized tissue including a first layer and a second layer, the first layer comprising collagen generally aligned in a first direction, the second layer comprising a multi-directional network of collagen fibers and elastin;
a second sheet including a second decellularized tissue, the second decellularized tissue including collagen generally aligned in a second direction, the first direction and the second direction defining an angle therebetween;
a third sheet including a third decellularized tissue, the third decellularized tissue including collagen generally aligned in a third direction, the third direction being essentially the same as the first direction, the second sheet being between the first sheet and the third sheet; wherein
the first, second and third sheets are attached to one another.

2. The biocompatible multi-laminate, angle-ply construct of claim 1, wherein the angle is from about 25° to about 90°.

3. The biocompatible multi-laminate, angle-ply construct of claim 1, wherein the angle is about 25° or less.

4. The biocompatible multi-laminate, angle-ply construct of claim 1, wherein the second decellularized tissue comprises a first layer and a second layer, the first layer comprising collagen generally aligned in the second direction, the second layer comprising a multi-directional network of collagen fibers and elastin.

5. The biocompatible multi-laminate, angle-ply construct of claim 1, wherein two or more of the first, second, and third decellularized tissues are derived from the same source tissue.

6. The biocompatible multi-laminate, angle-ply construct of claim 1, wherein one or more of the first, second, and third decellularized tissues is decellularized pericardium.

7. The biocompatible multi-laminate, angle-ply construct of claim 1, wherein one or more of the first, second, and third decellularized tissues are crosslinked.

8. The biocompatible multi-laminate, angle-ply construct of claim 1, further comprising a hydrogel between at least the first and second sheet.

9. The biocompatible multi-laminate, angle-ply construct of claim 1, wherein the biocompatible construct is an annulus fibrosus patch.

10. The biocompatible multi-laminate, angle-ply construct of claim 1, wherein the biocompatible construct is a musculoskeletal graft.

11. The biocompatible multi-laminate, angle-ply construct of claim 1, wherein the biocompatible construct exhibits a biaxial burst pressure of about 2 megapascals or greater, an ultimate tensile strength of about 3 megapascals or greater, and/or an elastic modulus of from about 12 megapascals to about 24 megapascals.

12. The biocompatible multi-laminate, angle-ply construct of claim 1, wherein the third decellularized tissue comprises a first layer and a second layer, the first layer comprising collagen generally aligned in the third direction, the second layer comprising a multi-directional network of collagen fibers.

13. The biocompatible multi-laminate, angle-ply construct of claim 1, the first sheet having an average thickness of between 150 micrometers and 270 micrometers.

14. A method for forming a biocompatible construct, the method comprising:
locating a first sheet adjacent to a second sheet, the first sheet including a first decellularized tissue, the first decellularized tissue including a first layer and a second layer, the first layer comprising collagen generally aligned in a first direction, the second layer comprising a multi-directional network of collagen fibers and elastin, the second sheet including a second decellularized tissue, the second decellularized tissue including collagen generally aligned in a second direction, the first sheet and the second sheet being located adjacent to one another such that an angle is defined between the first direction and the second direction;
locating a third sheet adjacent to the second sheet such that the second sheet is between the first sheet and the third sheet, the third sheet including a third decellularized tissue, the third decellularized tissue including collagen generally aligned in a third direction, the third sheet being located such that the third direction and the first direction are essentially the same; and
attaching the first, second, and third sheets to one another.

15. The method of claim 14, the angle being from about 25° to about 90°.

16. The method of claim 14, the angle being about 25° or less.

17. The method of claim 14, further comprising decellularizing the first, second, and third tissues.

18. The method of claim 14, further comprising crosslinking one or more of the first, second, and third decellularized tissues.

19. The method of claim 14, wherein two or more of the first, second, and third decellularized tissues are derived from the same source tissue.

20. The method of claim 14, wherein one or more of the first, second, and third decellularized tissues is decellularized pericardium.

21. The method of claim 14, further comprising locating a hydrogel or a hydrogel precursor between at least the first and second sheets.

* * * * *